United States Patent
Nanaumi et al.

(10) Patent No.: US 12,186,105 B2
(45) Date of Patent: Jan. 7, 2025

(54) SUBJECT INFORMATION ACQUISITION APPARATUS, MAGNETIC RESONANCE IMAGING APPARATUS, SUBJECT INFORMATION ACQUISITION METHOD, AND STORAGE MEDIUM

(71) Applicants: CANON KABUSHIKI KAISHA, Tokyo (JP); CANON MEDICAL SYSTEMS CORPORATION, Tochigi (JP)

(72) Inventors: Ryuichi Nanaumi, Tokyo (JP); Kazuya Okamoto, Saitama (JP); Takafumi Ohishi, Yokohama (JP)

(73) Assignees: CANON KABUSHIKI KAISHA, Tokyo (JP); CANON MEDICAL SYSTEMS CORPORATION, Tochigi (JP)

( * ) Notice: Subject to any disclaimer, the term of this patent is extended or adjusted under 35 U.S.C. 154(b) by 333 days.

(21) Appl. No.: 17/643,047

(22) Filed: Dec. 7, 2021

(65) Prior Publication Data
US 2022/0183630 A1   Jun. 16, 2022

(30) Foreign Application Priority Data
Dec. 14, 2020   (JP) .................. 2020-206972

(51) Int. Cl.
*A61B 5/00*   (2006.01)
*A61B 5/055*   (2006.01)
*G01R 33/567*   (2006.01)

(52) U.S. Cl.
CPC .............. *A61B 5/721* (2013.01); *A61B 5/055* (2013.01); *G01R 33/5673* (2013.01); *G01R 33/5676* (2013.01)

(58) Field of Classification Search
CPC .... A61B 5/721; A61B 5/055; G06R 33/5673; G06R 33/5676
See application file for complete search history.

(56) References Cited

U.S. PATENT DOCUMENTS

| 8,144,327 B2 | 3/2012 | Nakajima et al. |
| 8,300,224 B2 | 10/2012 | Nakajima et al. |

(Continued)

FOREIGN PATENT DOCUMENTS

| JP | 2007-61439 A | 3/2007 |
| JP | 2019-115465 A | 7/2019 |

(Continued)

*Primary Examiner* — Joel F Brutus
(74) *Attorney, Agent, or Firm* — VENABLE LLP

(57) ABSTRACT

A subject information acquisition apparatus, comprises: a signal generation unit configured to generate a high-frequency signal corresponding to each of the frequencies; an acquisition unit configured to acquire a plurality of detection signals based on at least one of a reflection signal and a transmission signal; a signal selection unit configured to select at least one detection signal from the plurality of detection signals based on an index value of the plurality of detection signals; a coupling amount detecting unit configured to detect a coupling amount of near-field coupling due to an electric field between the antenna and the subject based on a detection signal; and a displacement detecting unit configured to generate a displacement signal indicating a displacement of the subject based on the coupling amount.

28 Claims, 17 Drawing Sheets

(56) References Cited

U.S. PATENT DOCUMENTS

| | | |
|---|---|---|
| 9,566,006 B2 | 2/2017 | Nanaumi |
| 9,737,216 B2 | 8/2017 | Nanaumi |
| 10,064,557 B2 | 9/2018 | Nanaumi et al. |
| 10,531,798 B2 | 1/2020 | Nanaumi et al. |
| 2007/0083125 A1 | 4/2007 | Ouchi |
| 2014/0303473 A1 | 10/2014 | Nanaumi et al. |
| 2014/0306706 A1* | 10/2014 | Lazar .................. G01R 33/56 324/309 |
| 2016/0184133 A1 | 6/2016 | Miyasato et al. |
| 2017/0063143 A1* | 3/2017 | Hoarau ................ A41F 9/002 |
| 2017/0311927 A1 | 11/2017 | Yao et al. |
| 2018/0353140 A1 | 12/2018 | Speier |
| 2019/0041476 A1* | 2/2019 | Otake ................ G01R 33/343 |
| 2019/0183349 A1 | 6/2019 | Miyasato et al. |
| 2019/0331745 A1* | 10/2019 | Chen ................ G01R 33/3628 |
| 2020/0085345 A1 | 3/2020 | Nanaumi et al. |
| 2020/0315574 A1 | 10/2020 | Nanaumi et al. |
| 2020/0341083 A1* | 10/2020 | Ohishi ................ A61B 5/055 |
| 2021/0298629 A1* | 9/2021 | Ohishi ............ G01R 33/34038 |

FOREIGN PATENT DOCUMENTS

| | | |
|---|---|---|
| JP | 2019-208876 A | 12/2019 |
| JP | 2020-151458 A | 9/2020 |

* cited by examiner

FIG. 4
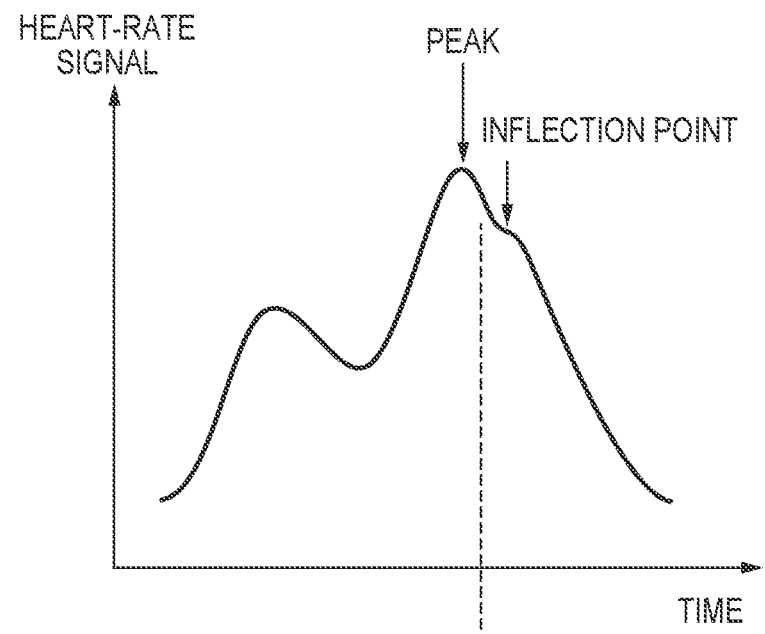
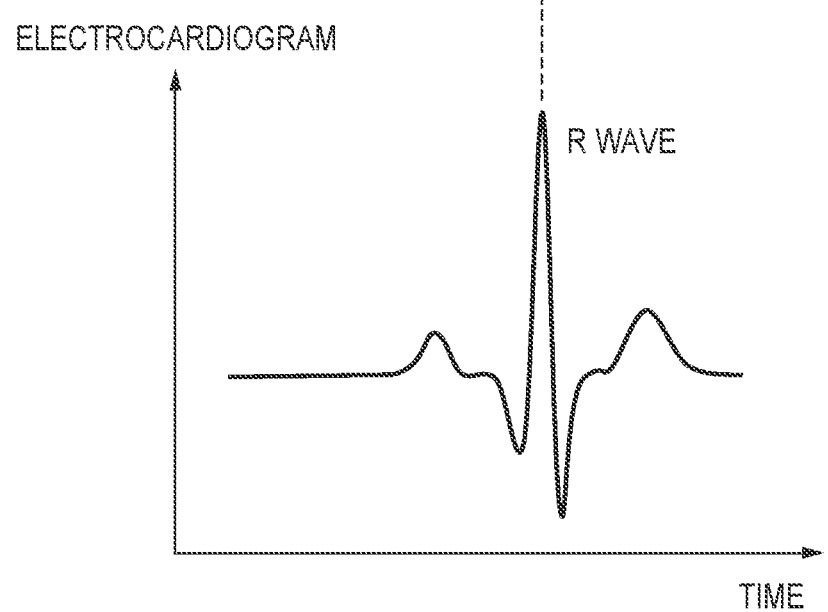

SUBJECT INFORMATION ACQUISITION APPARATUS, MAGNETIC RESONANCE IMAGING APPARATUS, SUBJECT INFORMATION ACQUISITION METHOD, AND STORAGE MEDIUM

BACKGROUND OF THE INVENTION

Field of the Invention

The present invention is related to a subject information acquisition apparatus, a magnetic resonance imaging apparatus, a subject information acquisition method, and a storage medium.

Description of the Related Art

In imaging using a magnetic resonance imaging apparatus, data to be collected changes due to movement of the human body due to pulsation of the heart (heartbeat), respiration, or the like. With respect to heartbeat, for example, techniques are used in which an imaging technician attaches an electrode of an electrocardiometer to the human body, and adjusts the imaging timing using a signal outputted from the electrocardiometer, or corrects the collected data based on the signal of the electrocardiometer.

However, attaching an electrode to a human body is a burden on a patient, and may result in low work efficiency for an imaging technician. For this reason, a non-contact technique for acquiring subject information is desired not only for imaging using a magnetic resonance imaging apparatus, but also in a wide range of healthcare fields.

US-2018-353140 discloses a technique for detecting a movement of a subject using radio waves, which is a technique for generating a signal for body movement of the subject from pilot tone signals acquired from the subject.

However, in the technique described in US-2018-353140, when a plurality of pilot tone signals acquired from the subject include a low-precision pilot tone signal, the precision of the detected the movement of the subject may be low.

The present invention has been made in view of the above-mentioned problem, and provides a technique capable of detecting movement of a subject with high accuracy and acquiring information on the behavior and state of the subject with high accuracy.

SUMMARY OF THE INVENTION

According to one aspect of the present invention, there is provided a subject information acquisition apparatus, comprising: a signal generation unit configured to generate a high-frequency signal corresponding to each of the frequencies, wherein different frequencies are set; an acquisition unit configured to acquire a plurality of detection signals based on at least one of a reflection signal and a transmission signal by irradiating the high-frequency signal corresponding to each of the frequencies to a subject from at least one antenna; a signal selection unit configured to select at least one detection signal from the plurality of detection signals based on an index value of the plurality of detection signals; a coupling amount detecting unit configured to detect a coupling amount of near-field coupling due to an electric field between the antenna and the subject based on a detection signal selected in the signal selection unit; and a displacement detecting unit configured to generate a displacement signal indicating a displacement of the subject based on the coupling amount detected in the coupling amount detecting unit.

According to one aspect of the present invention, there is provided a subject information acquisition apparatus, comprising: a signal generation unit configured to generate a high-frequency signal based on a set frequency; an acquisition unit configured to acquire a plurality of detection signals based on a reflection signal or a transmission signal by irradiating the high-frequency signal to a subject from at least one antenna; a coupling amount detecting unit configured to detect a coupling amount of near-field coupling due to an electric field between the antenna and the subject based on the detection signal; a displacement detecting unit configured to generate a displacement signal indicating a displacement of the subject based on the coupling amount detected in the coupling amount detecting unit; and a signal correction unit configured to correct at least one of the detection signal and the displacement signal detected by the displacement detecting unit.

According to the present invention, movement of a subject can be detected with high accuracy, and information on the behavior and state of the subject can be acquired with high accuracy.

Further features of the present invention will become apparent from the following description of exemplary embodiments (with reference to the attached drawings).

BRIEF DESCRIPTION OF THE DRAWINGS

FIG. 4 is a view illustrating a heart-rate signal corresponding to one period in the detection signal.

DESCRIPTION OF THE EMBODIMENTS

Figure 1:
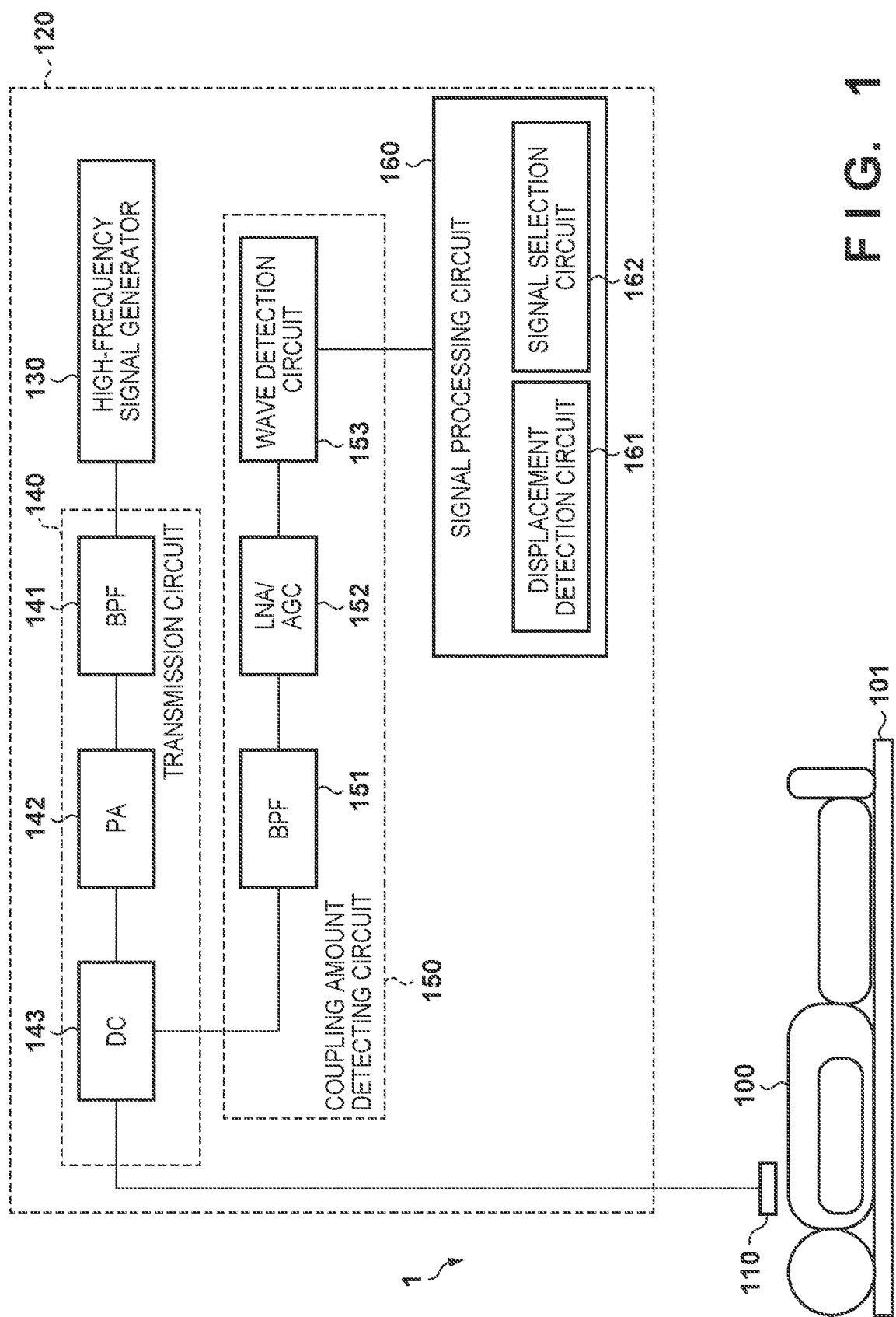
FIG. 1 is a diagram schematically showing a configuration of a subject information acquisition apparatus according to a first embodiment.

Hereinafter, an embodiment will be described in detail with reference to the accompanying drawings. Note that the following embodiments do not limit the invention according to the scope of the appended claims. In the embodiments, a plurality of features are described. However, not all the plurality of features are necessarily essential to the present invention, and the plurality of features may arbitrarily be combined. In addition, the same reference numerals denote the same or similar configurations in the accompanying drawings, and a repetitive description will be omitted.

Hereinafter, embodiments will be described in detail with reference to the attached drawings. Note, the following embodiments are not intended to limit the scope of the claimed invention. Multiple features are described in the embodiments, but limitation is not made an invention that requires all such features, and multiple such features may be combined as appropriate. Furthermore, in the attached drawings, the same reference numerals are given to the same or similar configurations, and redundant description thereof is omitted.

The present invention relates to a technique for detecting high-frequency reflections incident on the antenna installed on the subject, and generating and acquiring information on a state and a behavior of the subject, and can be regarded as a subject information acquisition apparatus, a control method thereof, or a subject information acquisition method or a signal processing method. The present invention can also be regarded as a program for causing an information processing apparatus including hardware resources such as a CPU to execute the subject information acquisition method and the signal processing method, or as a storage medium storing such a program. Furthermore, the invention can be regarded as a magnetic resonance imaging apparatus including these.

First Embodiment

Configuration of Subject Information Acquisition Apparatus

FIG. 1 is a diagram schematically showing a configuration of a subject information acquisition apparatus according to a first embodiment. The subject information acquisition apparatus 1 includes an antenna 110 and an apparatus main body 120 constituting the subject information acquisition apparatus 1.

The antenna 110 is a configuration of an antenna apparatus. In the present embodiment, since the subject information acquisition apparatus 1 in principle has one antenna, the antenna apparatus is configured by a single antenna. In the embodiment described later, the subject information acquisition apparatus 1 may include a plurality of antennas, and in this case, the antenna apparatus is configured by a plurality of antennas. The antenna apparatus (irradiation unit) irradiates the subject with a high-frequency signal from at least one antenna.

The measurement target of the subject information acquisition apparatus 1 is a subject 100, and the subject information acquisition apparatus 1 mainly aims to acquire movement of the subject 100 due to heart rate, respiration, or the like. As the subject 100, for example, a site of a living body, specifically, a heart, a lung, an abdomen in a human body or an animal, or a vicinity thereof, is assumed. However, the present invention is not necessarily limited to such sites, and any site where the movement of the subject 100 occurs can be targeted.

Figure 2:
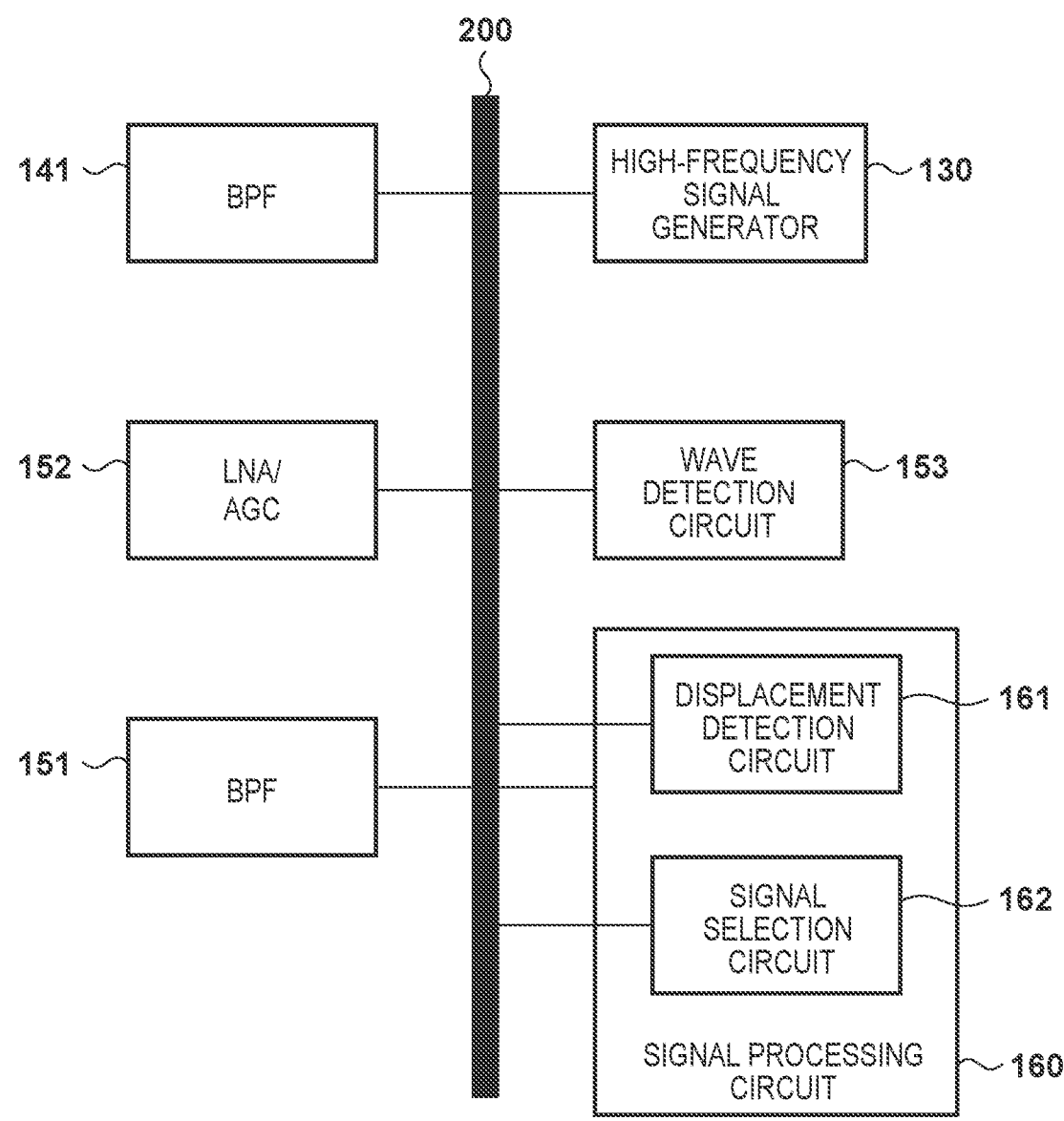
FIG. 2 is a diagram schematically showing the connection relationship of the constituent elements of the subject information acquisition apparatus.

FIG. 2 is a diagram schematically showing the connection relationship of the constituent elements of the apparatus main body 120. Each component of the apparatus main body 120 is interconnected via a bus 200 as in FIG. 2. Each component of the apparatus main body 120 can exchange information via the bus 200. The signal processing circuit 160 (signal processing unit) functions as a control unit to control the operation of each component of the apparatus main body 120 via the bus 200. Further, the signal processing circuit 160 holds a program in which a subject information acquisition method to be described later is recorded in an internal memory, and the signal processing circuit 160 can read the program from the memory, control each component of the apparatus main body 120, and cause the subject information acquisition apparatus 1 to execute the subject information acquisition method.

A power amplifier (PA) 142 or a directional coupler (DC) 143, and the antenna 110 for which settings are seldom changed after operating characteristics have been set and for which operation is passive are not explicitly described in FIG. 2, but in the case where active control by the apparatus main body 120 is required, these may be connected to the bus 200.

Antenna 110

The antenna 110 is disposed close to the subject 100, which is a human body. The antenna 110 does not need to be directly attached to the skin of the subject 100 as in the case of an electrode of an electrocardiometer, and may be placed on the clothing of the subject 100, for example. Although FIG. 1 shows an example in which the antenna 110 is disposed on the chest of the subject 100 who is lying on a top board 101 of the bed, a posture of the subject when the antenna 110 is arranged and the site of the subject where the antenna 110 is disposed are not limited to the example shown in FIG. 1. For example, the antenna 110 may be disposed on the chest or the back of the subject in a standing position, or may be disposed on the chest or the back of the subject in a sitting position, for example, during driving of a vehicle.

Apparatus Main Body 120

The apparatus main body 120 includes, as components, a high-frequency signal generator 130, a transmission circuit 140, a coupling amount detecting circuit 150, and a signal processing circuit 160.

High-Frequency Signal Generator 130

The high-frequency signal generator 130 (signal generation unit) generates a high-frequency signal of continuous waves based on a predetermined frequency. The frequency of the high-frequency signal is not particularly limited, but a frequency, such as one in the VHF band and UHF band, for example, is selected using the dimensions and the like of the antenna 110. For example, it is possible to set different frequencies in the high-frequency signal generator 130 (signal generation unit) and generate a high-frequency signal corresponding to the respective frequencies.

Transmission Circuit 140

The transmitting circuit 140, after causing the high-frequency signal generated by the high-frequency signal generator 130 to pass through a band-pass filter (BPF) 141, amplifies the signal to a predetermined power by a power amplifier (PA) 142, and outputs the result to the antenna 110 via a directional coupler (DC) 143.

Coupling Amount Detecting Circuit 150

The coupling amount detecting circuit 150 (coupling amount detecting unit) has a function of detecting a coupling amount of near-field coupling due to an electric field between the subject 100 and the antenna 110, for example, and is configured to include a band-pass filter (BPF) 151, a low-noise amplifier (LNA/AGC) 152 with an automatic-gain adjusting function, and, a wave detection circuit 153. The coupling amount detecting circuit 150 functions as an acquisition unit, and acquires a plurality of detection signals based on a reflection signal or a transmission signal when the subject is irradiated with a high-frequency signal corresponding to respective frequencies from at least one antenna 110. Then, the coupling amount detecting circuit 150 detects the coupling amount of the near-field coupling due to the electric field between the antenna 110 and the subject 100 based on the acquired detection signal.

The high-frequency signal generator 130, the transmission circuit 140, and the coupling amount detecting circuit 150, for example, can be mounted on a printed circuit board which is housed in a single casing.

The high-frequency signal outputted from the directional coupler 143 of the transmission circuit 140 is inputted to the antenna 110, but a portion of the high-frequency signal is not directed to the subject 100 and bounces back (is reflected) at the input terminal of the antenna 110, returns to the directional coupler 143, and branches into the coupling amount detecting circuit 150.

The coupling amount detecting circuit 150 measures the magnitude of the reflection signal from the antenna 110 by detecting the signal (reflection signal) output from the branch terminal of the directional coupler 143 by the wave detection circuit 153. Here, the magnitude of the reflection signal varies in accordance with the distance between the antenna 110 and the subject 100, and a change in the state of the subject 100 included in the electric field created by the antenna 110, such as a change in the shape or a change in the composition of inside or outside of the subject due to heartbeat or respiration. For example, as the subject 100 and the antenna 110 approach each other, the subject 100 absorbs a large amount of power from the antenna 110, and the reflected power decreases (i.e., the coupling amount of the near-field coupling becomes large).

On the other hand, when the subject 100 and the antenna 110 are separated from each other, the opposite occurs, i.e., the coupling amount of the near-field coupling becomes small. That is, the coupling amount detecting circuit 150 detects the coupling amount of the near-field coupling based on the magnitude of the reflection signal.

Although the above describes a configuration in which the reflection signal of the antenna 110 is inputted to the coupling amount detecting circuit 150 by the directional coupler 143, but configuration may be taken to make the antenna 110 a transmission-only antenna, and have a reception-only antenna (not shown) in addition to the antenna 110, and to input the output (transmitted signal) of the reception-only antenna to the band-pass filter 151. In this case, configuration may be such that the directional coupler 143 is removed from the configuration, and the output of the reception-only antenna (transmitted signal) may be configured to be inputted to the band-pass filter 151. As shown in FIG. 1, the reception-only antenna may be disposed on the same side as the antenna 110 with respect to the front side of the subject 100, or may be disposed on the back side of the subject 100 (e.g., inside the top board 101 of the bed). Similar to the case of the reflection signal, the magnitude of the transmission signal changes in accordance with a change in the distance between the subject 100 and the two antennas and a change in the state of the subject 100 in the electric field between the two antennas. That is, the coupling amount detecting circuit 150 detects the coupling amount of the near-field coupling based on the magnitude of the transmission signal. Thereafter, the signal by which the reflection signal or transmitted signal is detected is referred to as a detection signal.

Also, in the present invention, it is possible to use a reflection signal that reflects back from the input terminal and a transmission signal between a plurality of antennas among the high-frequency signals inputted to the input terminal of the antenna 110. In the case of using the transmission signal, there is the possibility that the electromagnetic waves that propagate through the subject 100 will be detected as a result, but the frequency characteristics of the antenna 110 change with the distance between the subject 100 and the antenna 110.

Note that there are various methods for detecting the change in the state of the subject 100 of the present invention, and there is no limitation to the embodiment above.

Signal Processing Circuit 160

The signal processing circuit 160 has a displacement detection circuit 161 (displacement detecting unit) and a signal selection circuit 162 (signal selection unit). The signal processing circuit 160 is typically configured by an element such as a CPU, a GPU, or an A/D converter, a circuit such as an FPGA, an ASIC, or the like. Further, the signal processing circuit 160 may be configured as a dedicated printed circuit board having a processor, or may be configured as an information processing apparatus such as a personal computer or a tablet terminal device having a display. The signal processing circuit 160 may be such that it is not only composed of only one element or circuit, but rather a plurality of elements and circuits. In addition, any of the elements or circuits may execute the respective processes performed in the subject information acquisition method. Incidentally, the signal processing circuit 160 has a non-transitory recording medium, and each process performed in the subject information acquisition method can be stored as a program that the signal processing circuit 160 executes itself.

Displacement Detection Circuit 161

Figure 3:
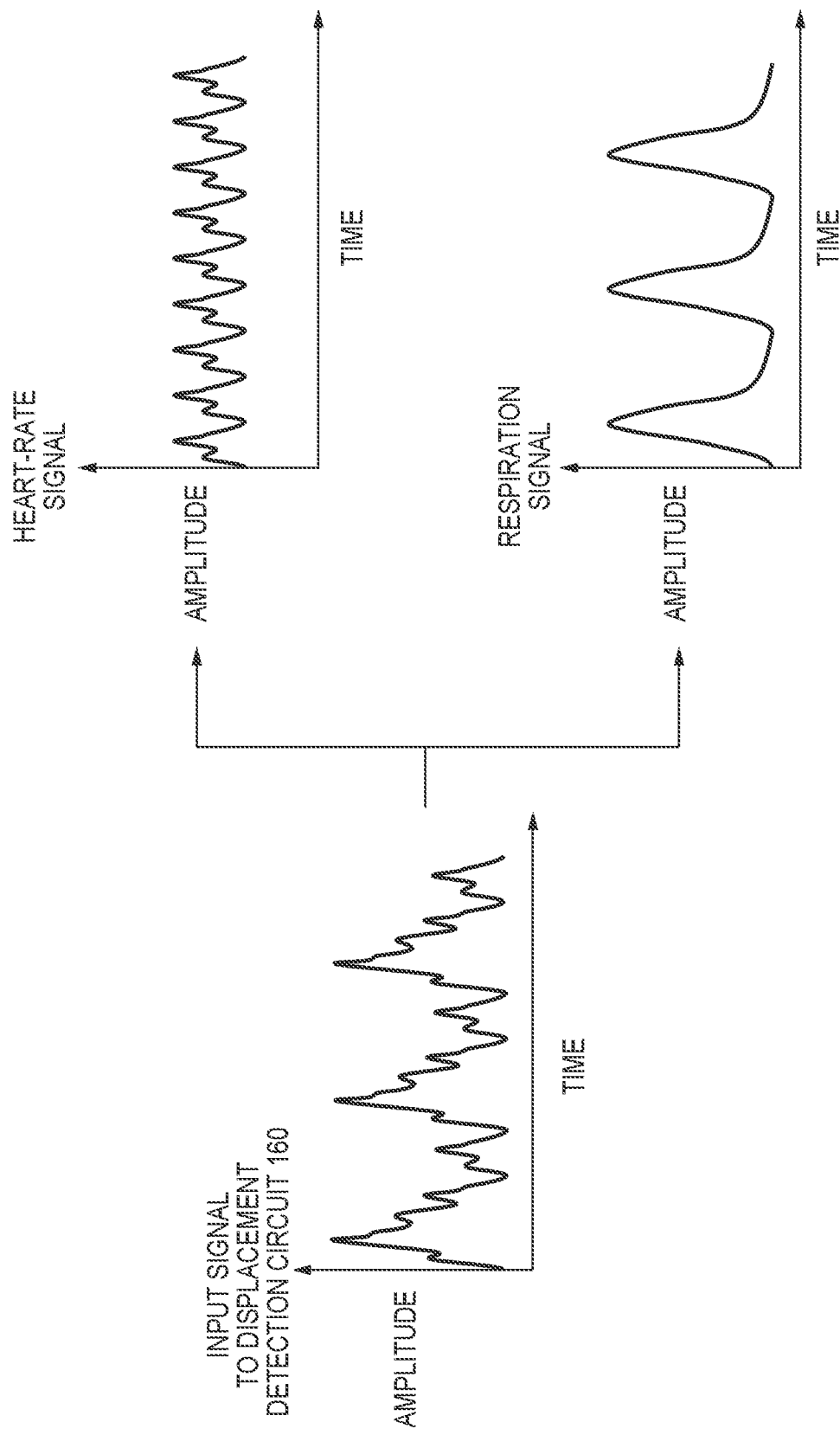
FIG. 3 is a diagram showing a detection signal, an extracted respiration signal, and a heart-rate signal.

The displacement detection circuit 161 extracts a signal (displacement signal) corresponding to a predetermined movement of the subject 100 from the detection signal detected by the wave detection circuit 153 based on the coupling amount of the near-field coupling (for example, a change in the coupling amount of the near-field coupling). The displacement signal extracted by the displacement detection circuit 161 is, for example, a signal corresponding to movement of the subject 100 due to respiration (respiration signal), a signal corresponding to movement of the subject 100 due to heartbeat (heart-rate signal), a signal corresponding to blinking, a signal corresponding to nodding, a signal corresponding to convulsion, or the like. As a process of extracting these signals (displacement signals), the displacement detection circuit 161 can use Fourier transform, short-time Fourier transform, wavelet transform, an infinite impulse response filter, a finite impulse response filter, a Kalman filter, principal component analysis, independent component analysis, a neural network or the like. FIG. 3 shows an example of the detection signal detected by the wave detection circuit 153, i.e., the input signal to the displacement detection circuit 161, and the respiration signal and the heart-rate signal are extracted from the detection signal as displacement signals.

The signal processing circuit 160 may display an extracted displacement signal as a waveform on a display or the like, or may acquire and display a respiration rate, a respiration cycle, a heart rate, a heartbeat cycle, or the like by analyzing the displacement signal. Further, the signal processing circuit 160 may detect the presence or absence of an abnormality in respiration or heartbeat from a waveform, a respiration rate, a heart rate, or the like. Similarly, blinking, nodding, convulsions, and the like of the subject 100 may be detected. Based on the detected information of the subject 100, the signal processing circuit 160 can control the apparatus for inspecting the subject 100 to synchronize with the movement, give a warning to the subject 100 or a third party, or provide feedback to a machine or a vehicle operated by the subject 100 to enhance safety.

Signal Selection Circuit 162

The signal selection circuit 162, based on an index value of the plurality of acquired detection signals corresponding to different frequencies set in the high-frequency signal generator 130, selects at least one detection signal from the plurality of detection signals. Here, the signal selection circuit 162, based on an index value calculated for each of the plurality of detection signals, selects an index value signal evaluated to be of high accuracy (detection signal) as a signal well-suited to acquiring the subject information, and selects the frequency of the high-frequency signal that was set in the high-frequency signal generator 130 when that detection signal was acquired. That is, the signal selection circuit 162 selects a signal well-suited for acquiring subject information (detection signal) and the frequency of the high-frequency signal corresponding to the detection signal based on the index values calculated for each of the plurality of detection signals.

Case Where a Correlation Value that Correlates With a Template Signal is Used as the Index Value First, processing in which a correlation value (a similarity) that correlates with a template signal indicating a reference signal waveform is initially used as an index (selection index) for the selection of the detection signal by the signal selection circuit 162 will be described. The signal selection circuit 162 using a similarity between a template signal indicating a reference signal waveform and a plurality of detection signals acquired in correspondence with different frequencies set in the high-frequency signal generator 130, selects, as the index value, at least one detection signal from a plurality of detection signals based on the similarity.

FIG. 4 is a view illustrating an example of a heart-rate signal corresponding to one period in the detection signal. When compared to an electrocardiogram of the same time phase as the heart-rate signal, for example, the peak or inflection point of the heart-rate signal is located in the vicinity of an R wave of the electrocardiogram, and the heart-rate signal has temporal relationship to the waveform of the electrocardiogram. That is, if the heart-rate signal as shown in FIG. 4 can be acquired, the behavior and state of the heart can be grasped similarly to a conventional method in which an electrocardiogram is taken. The peak and inflection point of the heartbeat waveform are only examples, and other feature points may be used as long as they correspond to the movement of the subject. Therefore, the accuracy of the detection signal including the heart-rate signal generated by the displacement detection circuit 161 can be evaluated by obtaining correlation values (similarity) with respect to an ideal template using the template signal (hereinafter, also referred to as the ideal template) as a reference heart-rate signal as shown in FIG. 4.

Figure 5:
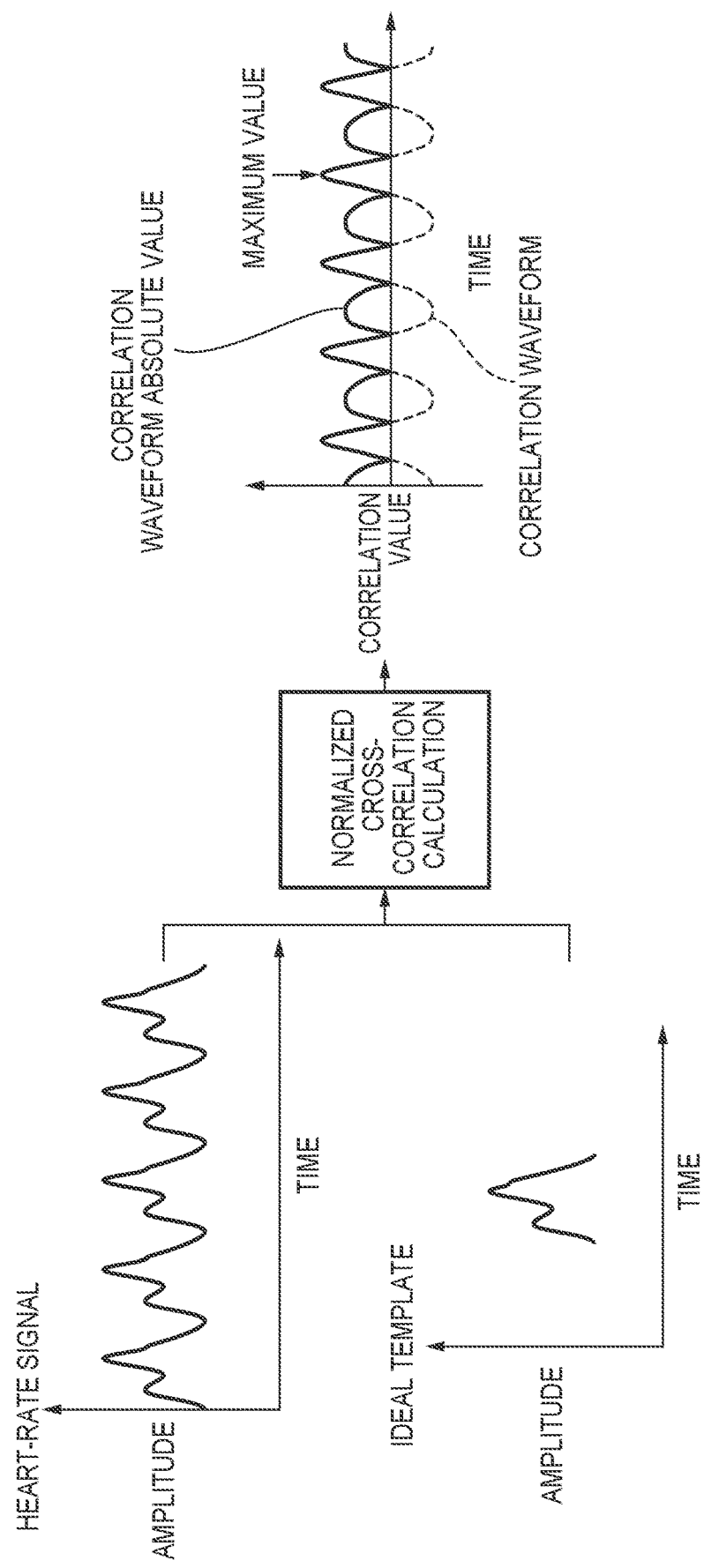
FIG. 5 is a diagram showing a process in which a correlation value with respect to an ideal template is used as an index value.

FIG. 5 is a diagram showing an outline of a process in which a correlation value (similarity) with respect to an ideal template is used as an index value. As shown in FIG. 5, the signal selection circuit 162 performs a normalized cross-correlation calculation on the heart-rate signal and the ideal template to generate a correlation waveform, and uses the maximum value of the absolute value of the correlation waveform as the index value. That is, the signal selection circuit 162 compares the index values calculated for each of a plurality of detection signals, and evaluates the heart-rate signal (the detection signal including the heart-rate signal) to be more accurate the larger an index value for similarity to the ideal template is. A plurality of detection signals are each for different settings of the frequency of the high-frequency signal, and a frequency of the high-frequency signal for which a detection signal of an index value evaluated to be of high accuracy was acquired is selected, and the high-frequency signal generator 130 generates a high-frequency signal based on the frequency selected by the signal selection circuit 162. As a result, measurement can be performed using a detection signal that is well-suited to acquiring subject information.

Since the heart-rate signal (a detection signal including the heart-rate signal) may have a shape in which the ideal template is inverted depending on the frequency of the high-frequency signal and the characteristics of the subject 100, the signal selection circuit 162 uses the absolute value of the correlation waveform in the signal processing. The present invention is not limited to such signal processing, and the signal selection circuit 162 may, before taking the absolute value of the correlation waveform, respectively calculate the average value of the maximum value and the average value of the minimum value of the correlation waveform, and use the larger absolute value as the index value, and the index value may be anything as long as it reflects similarity to the ideal template.

In the example shown in FIG. 5, a normalized cross-correlation calculation is used, but it is also possible to use any calculation method that can calculate similarity to the ideal template, such as a sum of absolute differences (SAD) or a sum of squared differences (SSD). Note that the ideal template is not limited to that of FIG. 4, and any signal that reflects a behavior or state of the heart, or a predetermined body movement may be used. Alternatively, the cycle of the heart-rate signal may be detected, and the ideal template may be enlarged or reduced in the time direction in accordance with the detection cycle.

Case Where the Signal-To-Noise Ratio of the Detection Signal is Used as the Index Value Next, a process of using an SN ratio (signal to noise ratio) of the detection signal as an index (selection index) for selecting the detection signal will be described.

Figure 6:
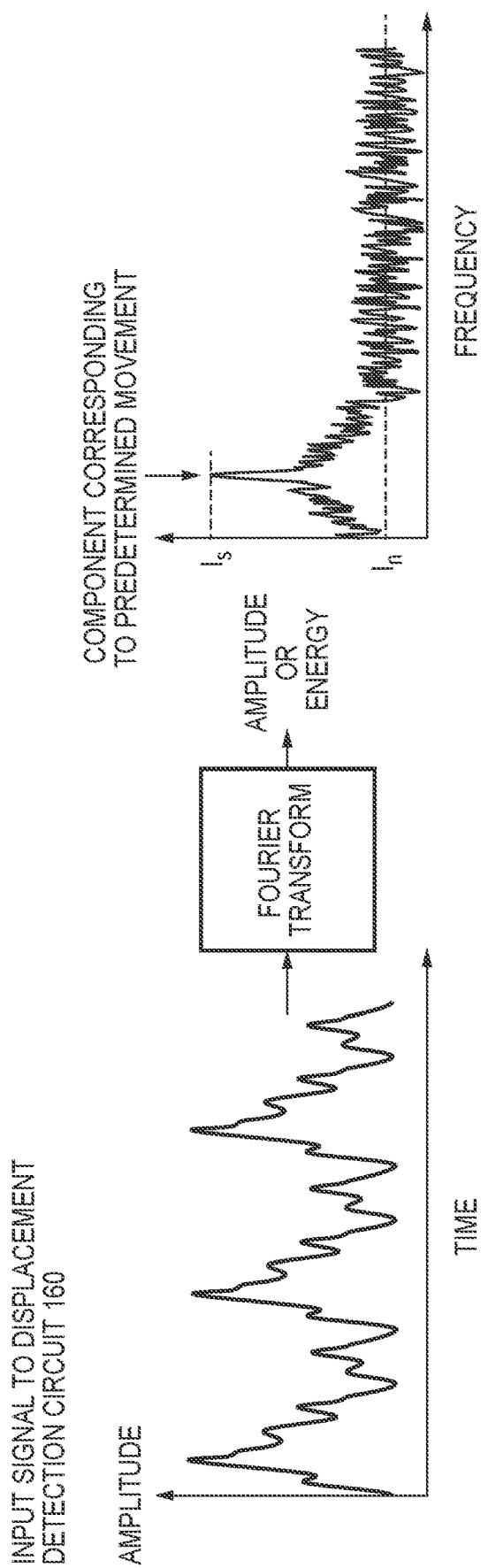
FIG. 6 shows an outline of a process for using a signal-to-noise ratio of a detection signal as an index value.

FIG. 6 shows an outline of a process for using a signal-to-noise ratio of a detection signal as an index value. The signal selection circuit 162 sets a signal ratio between a signal component indicating a coupling amount of a near-field coupling corresponding to a predetermined movement of the subject 100 and a noise signal component to be an index value, and based on a signal ratio, in a plurality of detection signals acquired in correspondence to different frequencies set in the high-frequency signal generator 130, selects at least one detection signal from a plurality of detection signals. As shown in FIG. 6, the signal selection circuit 162 Fourier-transforms the detection signal (input signal to the displacement detection circuit 161), and sets the signal ratio (SN ratio) Is/In between the signal component (Is) corresponding to the predetermined movement of the subject 100 and the noise signal component (noise floor: In) as the index value. That is, the signal selection circuit 162 evaluates a better SN ratio as more accurate. For example, since the component corresponding to a heartbeat is around 1 [Hz] and the component corresponding to respiration is around 0.3 [Hz], peak component values around these frequencies may be defined as Is. The present invention is not limited to the Fourier transform and any method, such as wavelet transform or Kalman filter, may be used if an SN ratio can be acquired.

The signal selection circuit 162, as described above, calculates an index value for selecting a detection signal from a plurality of detection signals, selects a signal (detection signal) for which the index value is large, and outputs the frequency of the high-frequency signal corresponding to the detection signal as the selection result. The signal selection circuit 162 outputs, as a selection result, an index for identifying a signal (detection signal) for which the index value is large among the plurality of detection signals, for example, and the selected signal (detection signal).

The signal selection circuit 162 selects the frequency of the high-frequency signal corresponding to the selected detection signal, and sets the frequency selected in the high-frequency signal generator 130. The high-frequency signal generator 130 generates a high-frequency signal based on the frequency set by the signal selection circuit 162. The displacement detection circuit 161 generates a displacement signal indicating the displacement of the subject 100 based on the coupling amount of the near-field coupling detected by the coupling amount detecting circuit 150.

Method of Acquiring Subject Information

Figure 7:
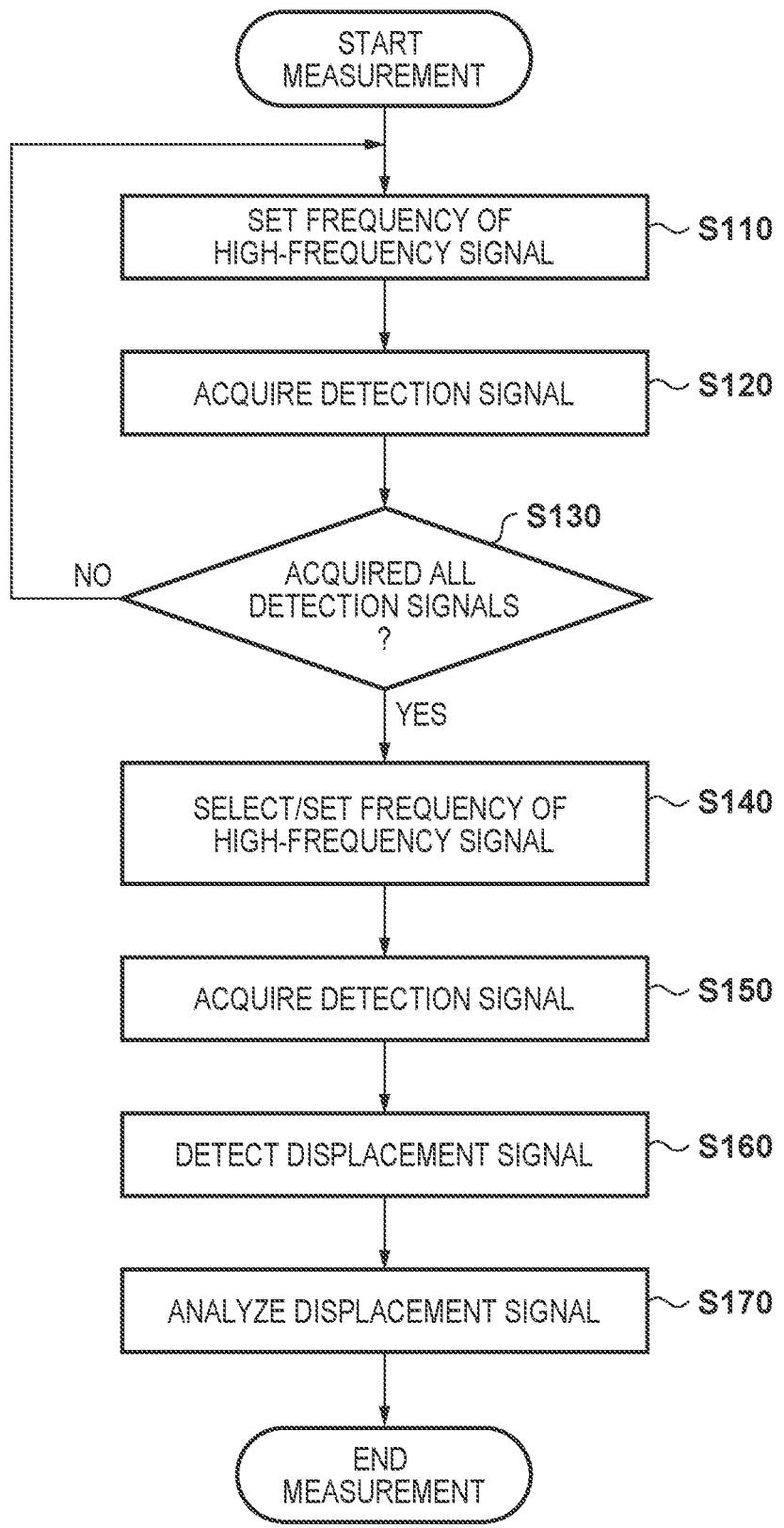
FIG. 7 is a diagram showing a processing flow in the first embodiment.

FIG. 7 is a diagram showing a processing flow in the first embodiment, and each step of the method of acquiring the subject information according to the present embodiment will be described with reference to FIG. 7. Incidentally, the signal processing circuit 160 executes each step by controlling the operation of each configuration of the apparatus main body 120.

Step S110: Step of Setting the High-Frequency Signal Frequency

In this step, the signal processing circuit 160 sets, to the high-frequency signal generator 130, the frequency of the high-frequency signal irradiated from the antenna 110 to the subject 100. The signal processing circuit 160 sets, to the high-frequency signal generator 130, a different frequency for each loop process that occurs at the condition branch of step S130. Typically, the frequency of the high-frequency signal can be set in a range from 100 [MHz] to 1 [GHz], but a suitable range for measurement of the subject information may be selected in accordance with the geometry of the antenna 110 and the site and composition of the subject 100. For example, in the case of a heart-rate signal or a respiration signal, the frequency of the high-frequency signal can be set in the range of 400 [MHz] to 650 [MHz]. Within this frequency range, the signal processing circuit 160 sets, to the high-frequency signal generator 130, a different frequency for each loop process. As the increment of the frequency, it is possible to set the frequency at intervals of a predetermined frequency (e.g., 5 [MHz]) in order to capture a high-precision detection signal, but it is also possible to set an interval larger than 5 [MHz] for the purpose of shortening the measurement time.

Step S120: Step of Acquiring a Detection Signal

In this step, a high-frequency signal of the frequency set in step S110 is irradiated from the antenna 110 to the subject 100 via the transmission circuit 140, and the coupling amount detecting circuit 150 acquires a detection signal based on the high-frequency signal. A duration over which to acquire the detection signal is a duration within which it is possible to calculate an index value in the signal selection circuit 162. By setting a shorter duration, the measurement time can be shortened. The signal processing circuit 160 stores the detection signal acquired from the coupling amount detecting circuit 150 in the internal storage medium.

Step S130: Step of Determining Whether a Detection Signal Has Been Acquired for All Frequencies In this step, the signal processing circuit 160 determines whether it has acquired a detection signal based on the high-frequency signal for all frequencies. When the acquisition of the detection signals is completed, the processing proceeds to step S140 (step S130—Yes), and when the acquisition of the detection signal has not completed, the processing returns to step S110 (step S130—No). When returning to the processing of step S110, a different frequency is set in step S110. Then, in step S120, the coupling amount detecting circuit 150 acquires a detection signal based on the high-frequency signal of the set frequency, and the signal processing circuit 160 stores the detection signal acquired from the coupling amount detecting circuit 150 and the frequency of the high-frequency signal corresponding to the detection signal in the internal storage medium. The signal processing circuit 160 performs such loop processing until a detection signal based on the high-frequency signal has been acquired for all frequencies. By the processing of step S110 to step S130, a plurality of detection signals for which the setting of the frequency of the high-frequency signal differs respectively are acquired.

Step S140: Step of Selecting/Setting the High-Frequency Signal Frequency

In this step, the signal selection circuit 162 calculates an index value for each of the plurality of detection signals having different frequencies of the high-frequency signal acquired in step S110 to step S130, selects a detection signal having the largest index value from the index values of the plurality of detection signals thus calculated, and selects the frequency of the high-frequency signal set to the high-frequency signal generator 130 when the detection signal was acquired. That is, the signal selection circuit 162 selects a signal well-suited for acquiring subject information (detection signal) and the frequency of the high-frequency signal corresponding to the detection signal based on the index values calculated for each of the plurality of detection signals. In this step, the signal selection circuit 162 may select the frequency of the high-frequency signal corresponding to one detection signal based on the magnitude of the index value from the calculated plurality of index values, and it is also possible to select a plurality of frequencies of the high-frequency signal corresponding to the highest ranked detection signals in the order of highest to lowest index values.

For example, when a principal component analysis or an independent component analysis is used in the detection process of the displacement signal in step S170, a plurality of frequencies of the high-frequency signal corresponding to the highest ranked detection signals in order of largest to smallest index values may be selected. The signal processing circuit 160 sets the frequency of the high-frequency signal selected by the signal selection circuit 162 to the high-frequency signal generator 130.

Incidentally, this step may be performed between step S120 and step S130, and rather than saving the detection signal in the storage medium in step S130, the index value may be acquired from the detection signal acquired in step S120, and the acquired index value may be saved in the storage medium. In this case, the signal selection circuit 162 may acquire the index values of the detection signals from the storage medium and select a single frequency of a high-frequency signal corresponding to a detection signal based on the magnitude of the index value, and the signal selection circuit may select a plurality of frequencies of the high-frequency signal corresponding to the highest ranked detection signals in order of the largest to the smallest index value of the detection signals. The signal processing circuit 160 sets a frequency selected by the signal selection circuit 162 to the high-frequency signal generator 130.

Step S150: Step of Acquiring a Detection Signal

In this step, the high-frequency signal of the frequency set in the high-frequency signal generator 130 in step S140 is irradiated from the antenna 110 via the transmission circuit 140 to the subject 100, the coupling amount detecting circuit 150 acquires a detection signal based on the high-frequency signal of the set frequency. The coupling amount detecting circuit 150 inputs the acquired detection signal to the displacement detection circuit 161 of the signal processing circuit 160.

Step S160: Step of Detecting a Displacement Signal

In this step, the displacement detection circuit 161 of the signal processing circuit 160 acquires a displacement signal corresponding to a predetermined movement of the subject 100 from the detection signal acquired in step S150.

Step S170: Step of Analyzing the Displacement Signal

In this step, the signal processing circuit 160 analyzes the displacement signal acquired by the displacement detection circuit 161 in step S160 to acquire information about the behavior and state of the subject 100.

It should be noted that, among the processing flows described with reference to FIG. 7, by executing the processing of step S150, step S160, and step S170 in parallel, the displacement signal may be acquired in real time to acquire information on the behavior and the state of the subject 100.

As described above, according to the present embodiment, by selecting the frequency of a high-frequency signal well-suited to acquiring the subject information, it is possible to perform measurement with a detection signal well-suited to acquiring the subject information, and it is possible to detect movement with high accuracy and to acquire information related to the behavior and state of the subject with high accuracy.

Second Embodiment

In the present embodiment, a subject information acquisition apparatus having a configuration for correcting a detection signal and a displacement signal will be described. Components identical to those of the first embodiment are denoted by the same reference numerals, and descriptions thereof are omitted.

Configuration of Subject Information Acquisition Apparatus

Figure 8:
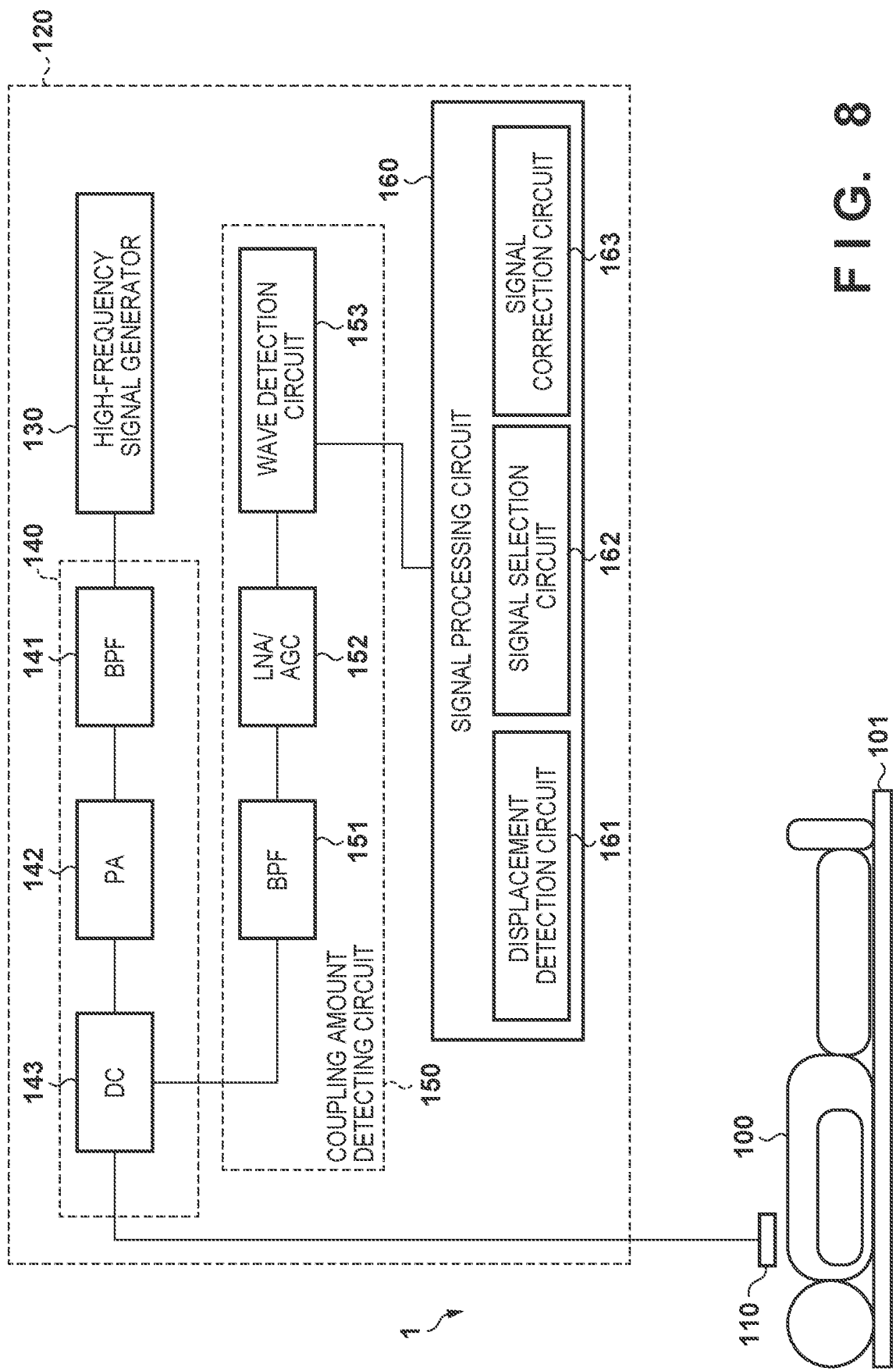
FIG. 8 is a diagram schematically showing a configuration of the subject information acquisition apparatus according to a second embodiment.
Figure 9:
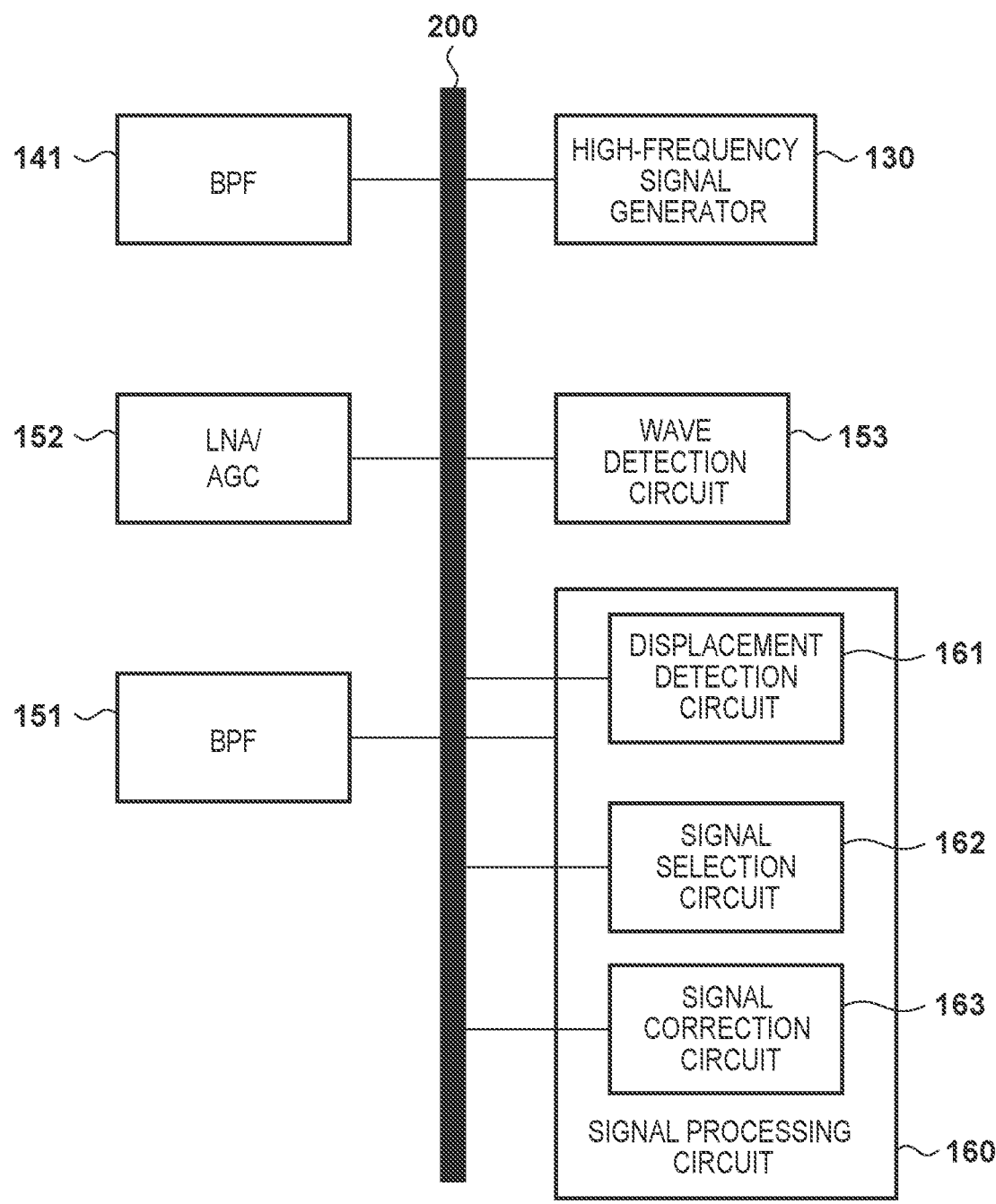
FIG. 9 is a diagram schematically showing a connection relationship of components in the apparatus main body of the second embodiment.

FIG. 8 is a diagram schematically showing a configuration of the subject information acquisition apparatus according to the second embodiment, and FIG. 9 is a diagram schematically showing a connection relationship of components in the apparatus main body 120 of the second embodiment. Similar to the connection relationship described in the first embodiment, as shown in FIG. 9, each component of the apparatus main body 120 can exchange information via the bus 200, and the signal processing circuit 160 controls operation of each component of the apparatus main body 120 via the bus 200. In the second embodiment, the signal processing circuit 160 differs from the connection relationship of the components described in the first embodiment (FIG. 2) in that it has a signal correction circuit 163 for correcting the detection signal and the displacement signal (signal correction unit).

Signal Correction Circuit 163

The signal correction circuit 163 corrects at least one of the detection signal selected by the signal selection circuit 162 and the displacement signal detected by the displacement detection circuit 161. Here, as an example of the inversion of the displacement signal (e.g., the heart-rate signal), a case where a correction for inverting the code of the displacement signal is performed in the signal correction circuit 163 will be described. The heart-rate signal may have a shape in which an ideal template is inverted depending on the frequency of the high-frequency signal and the characteristics of the subject 100.

In a case where the signal correction circuit 163 detected an inversion of the displacement signal, for example, the signal correction circuit 163 generates a non-inverted correction signal obtained by multiplying a correction value (−1) with the displacement signal. Thus, it is possible to suppress a decrease in analysis precision even when the signal processing circuit 160 analyzes the displacement signal in the case of non-inversion. For example, in the case of analysis processing for detecting a maximum value from the displacement signal, it may be impossible to detect that the maximum value is a minimum value when the displacement signal is inverted but possible to detect a maxima to be detected if it is a non-inverted correction signal.

Figure 10:
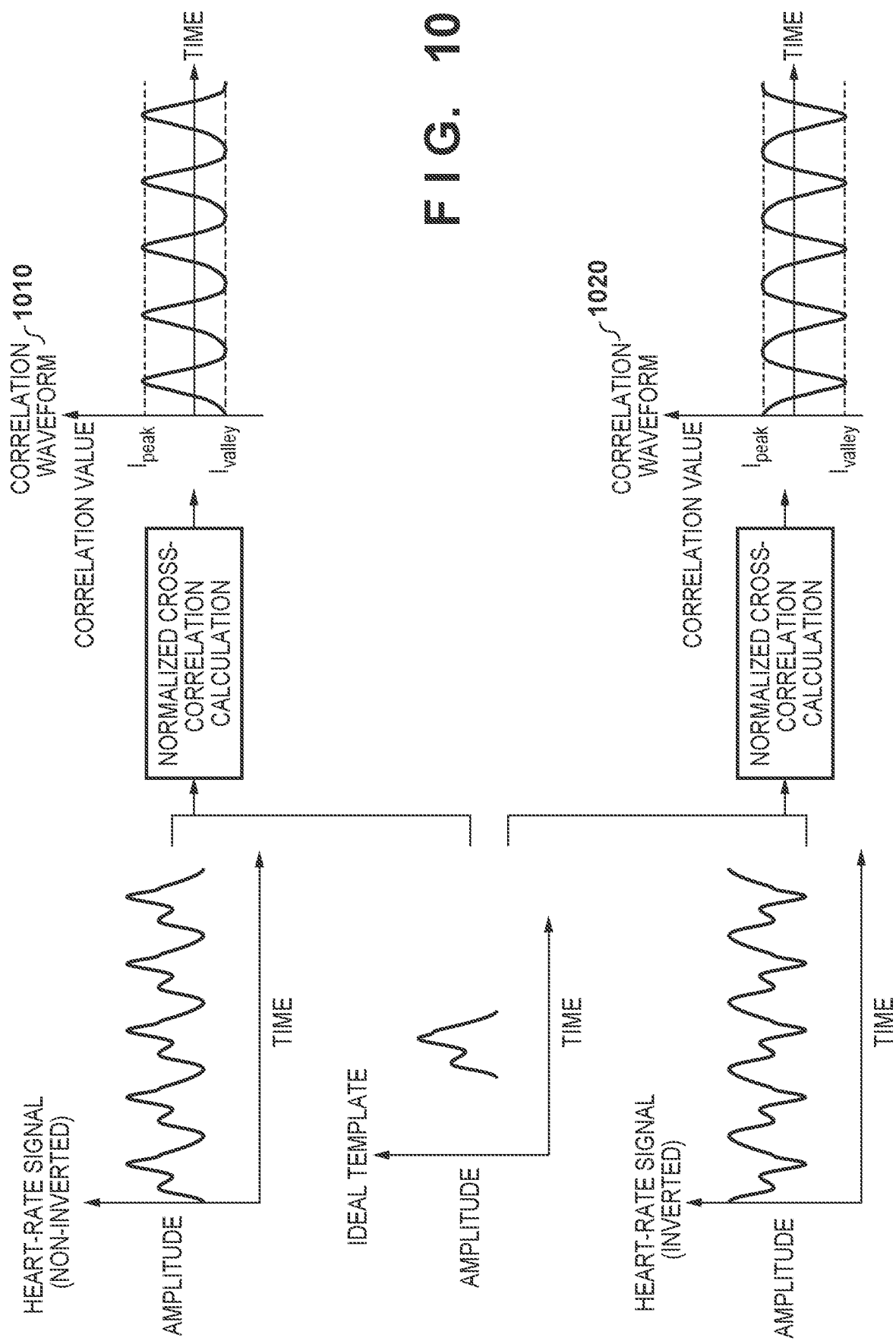
FIG. 10 shows an outline of a process of signal inversion detection.

FIG. 10 shows an outline of a process of signal inversion detection. As shown in FIG. 10, the signal correction circuit 163 respectively performs normalized cross-correlation calculation on the heart-rate signal (inverted or non-inverted) and the ideal template to generate a correlation waveform, and calculates a local maximum average value $I_{peak}$ and a local minimum average value $I_{valley}$. For a correlation waveform 1010 for non-inverted heart-rate signals, $|I_{peak}|>|I_{valley}|$, and for a correlation waveform 1020 when the heart-rate signals are inverted, $|I_{peak}|<|I_{valley}|$; therefore, it is possible for the signal correction circuit 163 to determine inversion and non-inversion of the signals from the magnitude relationship between $|I_{peak}|$ and $|I_{valley}|$.

If signal inversion occurs in the displacement signal and correction of the displacement signal is required, the signal correction circuit 163 multiplies a correction value (−1) with the displacement signal to produce a correction signal that is non-inverted.

Next, correction of the detection signal will be described. For example, even if the detection signal corresponds to the periodic movement of the subject 100, the detection signal may be subject to a disturbance or the like originating from the living body. The signal correction circuit 163 corrects for disturbances in the waveform in such detection signals. Here, correction of the detection signal will be described as an example of correction of the signal, but the signal correction circuit 163 can similarly perform the correction of a signal in relation to the displacement signal.

Figure 11:
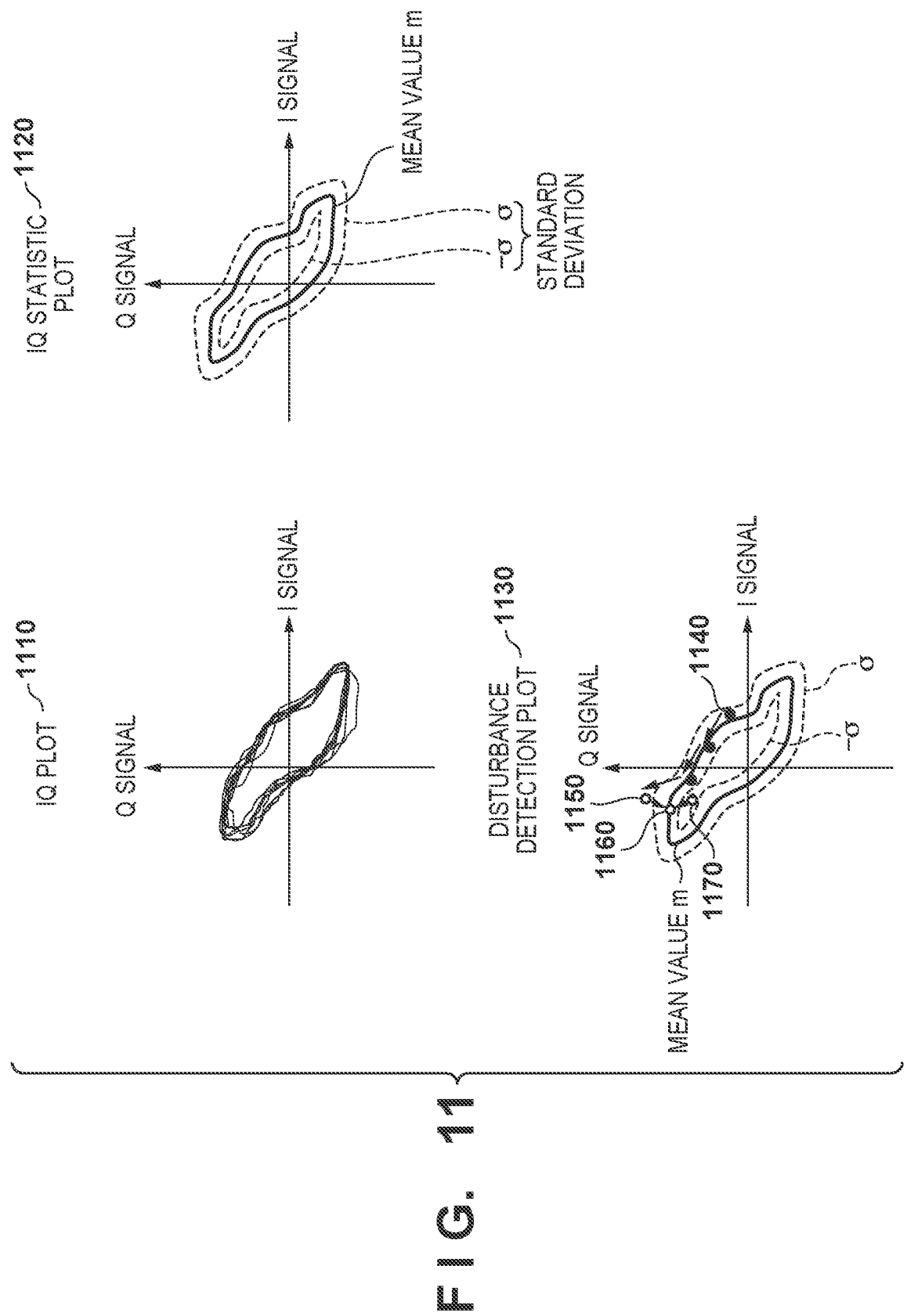
FIG. 11 shows an outline of a process of correcting a disturbance.

FIG. 11 is a diagram that illustrates an outline of processing for correcting a disturbance originating in a living body. An IQ plot 1110 of FIG. 11 is a diagram in which an In-phase signal (I signal) and Quadrature signal (Q signal) which are detected by the wave detection circuit 153 are plotted on in two-dimensional plane over a plurality of periods of a detection signal (e.g., the heart-rate signal). The length of a straight line connecting each point and the origin on the IQ plot 1110 represents the detection amplitude. The angle formed by the line connecting each point and the origin on the IQ plot 1110 and the I signal axis represents the detection phase.

An IQ statistic plot 1120 in FIG. 11 plots the mean value m (solid line) and standard deviation σ (dashed line) of the detection amplitude for each detection phase. Further, a disturbance detection plot 1130 of FIG. 11 is a diagram showing a state in which a disturbance is detected. Here, the signal correction circuit 163 performs statistical processing of the signal (detection signal, displacement signal), and if the value of the signal obtained by the statistical processing is outside of a condition regarding the reference value, corrects the value of the signal so as to satisfy the condition regarding the reference value. Since the detection amplitude for a black circle 1140 is within a reference value (within the standard deviation σ) in the disturbance detection plot, the signal correction circuit 163 determines that the disturbance is small, and does not perform correction of the signal.

On the other hand, since the value of a broken-line circle 1150 is outside of the condition regarding the detection amplitude of the reference value (standard deviation σ), the signal correction circuit 163 determines that the disturbance of the signal value indicated by the broken-line circle 1150 is larger than the reference value (standard deviation σ), and corrects the value of the signal (the value of the circle 1150 of the broken line) to be the average value m indicated by the solid-line white circle 1160 so as to satisfy the condition regarding the reference value, for example. In this way, the correction process by the signal correction circuit 163 can reduce the influence of disturbance in the signal. Incidentally, in addition to using the value of the reference value (standard deviation σ) as a reference for the criteria for determining whether to perform the correction process for reducing the influence of disturbance, the value of 2σ or 3σ may be used as the reference value.

An example in which the disturbance of the signal is determined to be larger than the reference value (standard deviation σ) is described in the disturbance detection plot 1130 of FIG. 11, but the present embodiment is not limited to this example. For example, if the standard deviation −σ is used as a reference value, and the disturbance of the signal is smaller than the reference value (standard deviation −σ), and is outside of a condition regarding the reference value (standard deviation −σ) (e.g., the circle 1170 of the broken line), the signal correction circuit 163 corrects the value of the signal (the value of the broken-line circle 1170) to become the value of the average value m indicated by white circle 1160 of the solid line, for example, so as to satisfy the condition regarding the reference value. In this way, the correction process by the signal correction circuit 163 can reduce the influence of disturbance in the signal. In addition to using the value of the standard deviation −σ as a reference, the value of −2σ or −3σ may be used as a reference.

A reference value other than the standard deviation (−σ, σ), such as an experimentally obtained arbitrary threshold value, may be adopted as criteria for determining the necessity of correction. Further, in the example shown in FIG. 11, the value of the broken-line circle 1150 which is outside of the condition regarding the reference value (standard deviation σ) is corrected to the average value m as the correction value (correction target value), but an arbitrary experimentally obtained correction value or a boundary value of the standard deviation σ may be adopted as a correction value (correction target value). Furthermore, it is also possible to perform correction using a frequency component of the displacement signal or the detection signal. For example, it is possible for the signal correction circuit 163 to deconvolve the frequency component of the displacement signal or the detection signal with a frequency component of an envisioned ideal signal waveform, and to perform correction by deconvolving the signal (displacement signal or the detection signal).

In the case of a heartbeat waveform, the frequency component as shown in FIG. 6 is deconvolved with the frequency component of an ideal template as shown in FIG. 4. Specifically, it is possible to perform a Fourier transform, perform a deconvolution, and then perform an inverse Fourier transform to obtain a corrected signal. It is also possible to generate a deconvolution waveform by inverse Fourier transform of the inverse of the frequency component of the ideal template, and to configure a deconvolution FIR filter from the deconvolution waveform and apply it to the displacement signal and the detection signal. In the above deconvolution, a Wiener filter can be used.

The displacement detection circuit 161 generates a displacement signal based on the signal corrected by the signal correction circuit 163, and the signal processing circuit 160 acquires information indicating movement of the subject based on the generated displacement signal.

Method of Acquiring Subject Information

Figure 12:
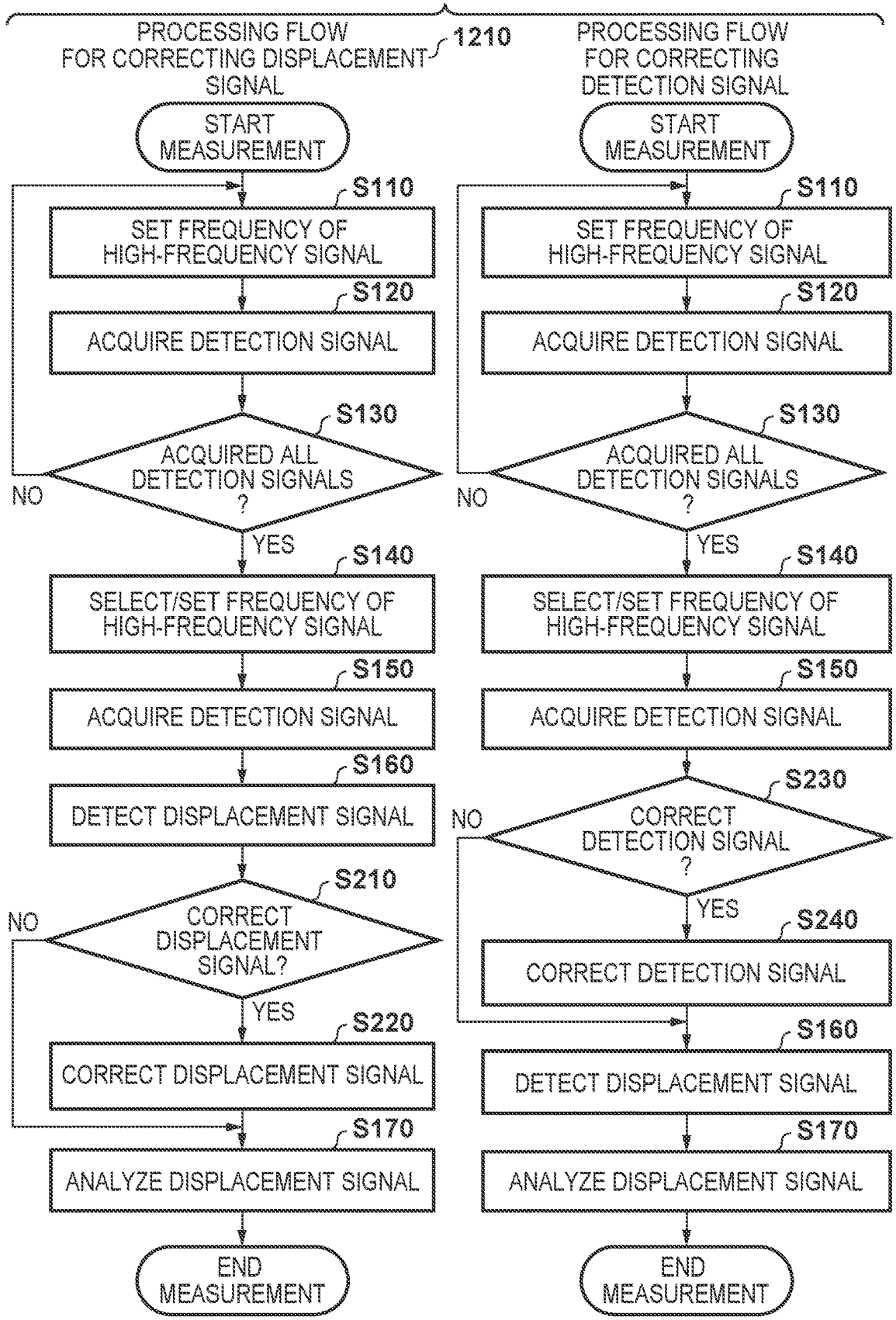
FIG. 12 is a diagram showing a processing flow in the second embodiment.

FIG. 12 is a diagram showing a processing flow in the first embodiment, and each step of the subject information acquisition method according to the present embodiment will be described with reference to FIG. 12. In FIG. 12, two types of processing flows are shown: a processing flow 1210 for correcting the displacement signal, and a processing flow 1220 for correcting the detection signal. Note that each step in the processing flow 1210 and the processing flow 1220 is executed by the signal processing circuit 160 controlling the operation of the respective components of the apparatus main body 120. Description of the same steps as those in the processing flow of the first embodiment (FIG. 7) is omitted.

First, a processing flow 1210 for correcting the displacement signal will be described. The processing of step S110 to step S160 is the same as in the processing flow of the first embodiment (FIG. 7).

Step S210: Step of Determining Whether to Correct the Displacement Signal

In this step, the signal correction circuit 163 determines whether to correct the displacement signal detected in step S160. The content of the correction of the displacement signal may be the inversion of the waveform in the displacement signal, for example. As described in FIG. 10, if an inversion occurs in the waveform of the displacement signal according to the magnitude relation between the local maximum average value $I_{peak}$ and the local minimum average value $I_{valley}$, the signal correction circuit 163 determines to correct the displacement signal (step S210—Yes), and the process proceeds to step S220.

Step S220: Step of Correcting a Displacement Signal

In this step, the signal correction circuit 163 multiplies a correction value (−1) with the displacement signal to generate a non-inverted correction signal. Then, in the next step (step S170), the signal processing circuit 160 analyzes the displacement signal corrected by the signal correction circuit 163 in step S220 to acquire information about the behavior and state of the subject 100.

On the other hand, in the determination process of step S210, if no inversion occurs in the waveform of the displacement signal, the signal correction circuit 163 determines that the displacement signal is not corrected (step S210—No), and the process proceeds to step S170. In this case, the signal processing circuit 160 analyzes the displacement signal acquired by the displacement detection circuit 161 in step S160 to acquire information about the behavior and state of the subject 100.

Next, a processing flow 1220 for correcting the detection signal will be described. The processing of step S110 to step S150 is the same as in the processing flow of the first embodiment (FIG. 7).

Step S230: Step of Determining Whether to Correct the Detection Signal

In this step, the signal correction circuit 163 determines whether to correct the detection signal acquired in step S150. The content of the correction of the detection signal may be disturbance of the waveform in the detection signal, for example. As described in FIG. 11, if the value of the waveform in the detection signal (e.g., the value of the circle 1150 of the broken line) is outside of a condition regarding the reference value (e.g., the standard deviation σ, the value 2σ or 3σ, any threshold obtained experimentally, etc.), the signal correction circuit 163 determines to correct the detection signal (step S230—Yes), and the process proceeds to step S240.

Step S240: Step of Correcting the Detection Signal

In this step, the signal correction circuit 163 corrects the detection signal to a predetermined correction value (e.g., the average value m of the signal, the boundary value of any correction value or standard deviation σ obtained experimentally, etc.). Then, in the next step (step S160), the displacement detection circuit 161 acquires the displacement signal corresponding to predetermined movement of the subject 100 from the detection signal corrected by the signal correction circuit 163 in step S240. Then, the signal processing circuit 160 analyzes the displacement signal acquired by the displacement detection circuit 161 in step S160 to acquire information about the behavior and state of the subject 100.

On the other hand, in the determination process of step S230, if no disturbance is detected in the waveform of the detection signal, the signal correction circuit 163 determines that the detection signal is not corrected (step S230—No), and the process proceeds to step S160. In this case, the signal processing circuit 160 acquires a displacement signal corresponding to a predetermined movement of the subject 100 from the detection signal acquired in step S150. Then, in step S170, the signal processing circuit 160 analyzes the displacement signal acquired by the displacement detection circuit 161 in step S160 to acquire information regarding the behavior and state of the subject 100.

Note that the correction of the signal is not limited to the above example, and in the processing flow 1210 for correcting the displacement signal, for example, the disturbance included in the displacement signal may be corrected in the same manner as the processing of the processing flow 1220. Also, in the processing flow 1220 for correcting the detection signal, the inversion of the waveform included in the detection signal may be corrected in the same manner as the processing of the processing flow 1210. That is, any correction may be performed as long as it is a correction to the detection signal acquired under a condition selected/set in step S140 or a displacement signal extracted therefrom. A waveform inversion and disturbance correction may also be combined.

Further, the processing of step S210 and step S220 may be executed in parallel with the processing of step S150 and step S160 and step S170, and the processing results may be outputted in real time. Similarly, the processing of step S230 and step S240 may be executed in parallel with the processing of step S150 and step S160 and step S170. Further, the processing of step S210 or step S230 may be executed prior to the processing of step S150 to determine in advance whether the correction is necessary or not, and the determination processing during the execution of the correction in real time may be omitted.

Variation

In the second embodiment, a configuration in which the signal correction circuit 163 corrects at least one of the detection signal and the displacement signal has been described. Here, the detection signal is a signal selected by the signal selection circuit 162 based on the index value of a plurality of detection signals. Further, a displacement signal indicating a displacement of a subject is a signal generated by the displacement detection circuit 161 based on the coupling amount of the near-field coupling by an electric field between the antenna 110 and the subject 100, and the coupling amount of the near-field coupling is detected based on the detection signal selected by the signal selection circuit 162. That is, the signal to be corrected by the signal correction circuit 163 (detection signal and displacement signal) is a signal acquired based on a selection process of the signal selection circuit 162.

Note that the processing of the signal correction circuit 163 is not limited to this example, and it is possible for the signal correction circuit 163 to correct at least one signal among the detection signal inputted to the coupling amount detecting circuit 150 (input detection signal) and the displacement signal, regardless of the selection process of the signal selection circuit 162. In this case, the high-frequency signal generator 130 (signal generation unit) generates a high-frequency signal based on a set frequency. The coupling amount detecting circuit 150 functions as an acquisition unit, and when high-frequency signals are irradiated to the subject 100 from at least one antenna 110, the coupling amount detecting circuit 150 acquires a detection signal (input detection signal) based on a reflection signal or a transmission signal from the subject 100.

Also, the coupling amount detecting circuit 150 (coupling amount detecting unit) detects a coupling amount of near-field coupling due to the electric field between the antenna 110 and the subject 100 based on the detection signal (input detection signal). The displacement detection circuit 161 generates a displacement signal indicating the displacement of the subject 100 based on the coupling amount of the near-field coupling detected by the coupling amount detecting circuit 150. The signal correction circuit 163 corrects at least one of the detection signal (input detection signal) and the displacement signal detected by the displacement detection circuit 161. Signal correction processing by the signal correction circuit 163 is the same as the processing described previously, and the displacement detection circuit 161 generates a displacement signal based on the signal corrected by the signal correction circuit 163.

As described above, according to the present embodiment, by performing correction on the detection signal and the displacement signal, movement of the subject can be detected with high accuracy, and information on the behavior and state of the subject can be acquired with high accuracy.

Third Embodiment

In the present embodiment, a subject information acquisition apparatus having a plurality of antennas will be described. Components identical to those of the first embodiment are denoted by the same reference numerals, and descriptions thereof are omitted.

Configuration of Subject Information Acquisition Apparatus

Figure 13:
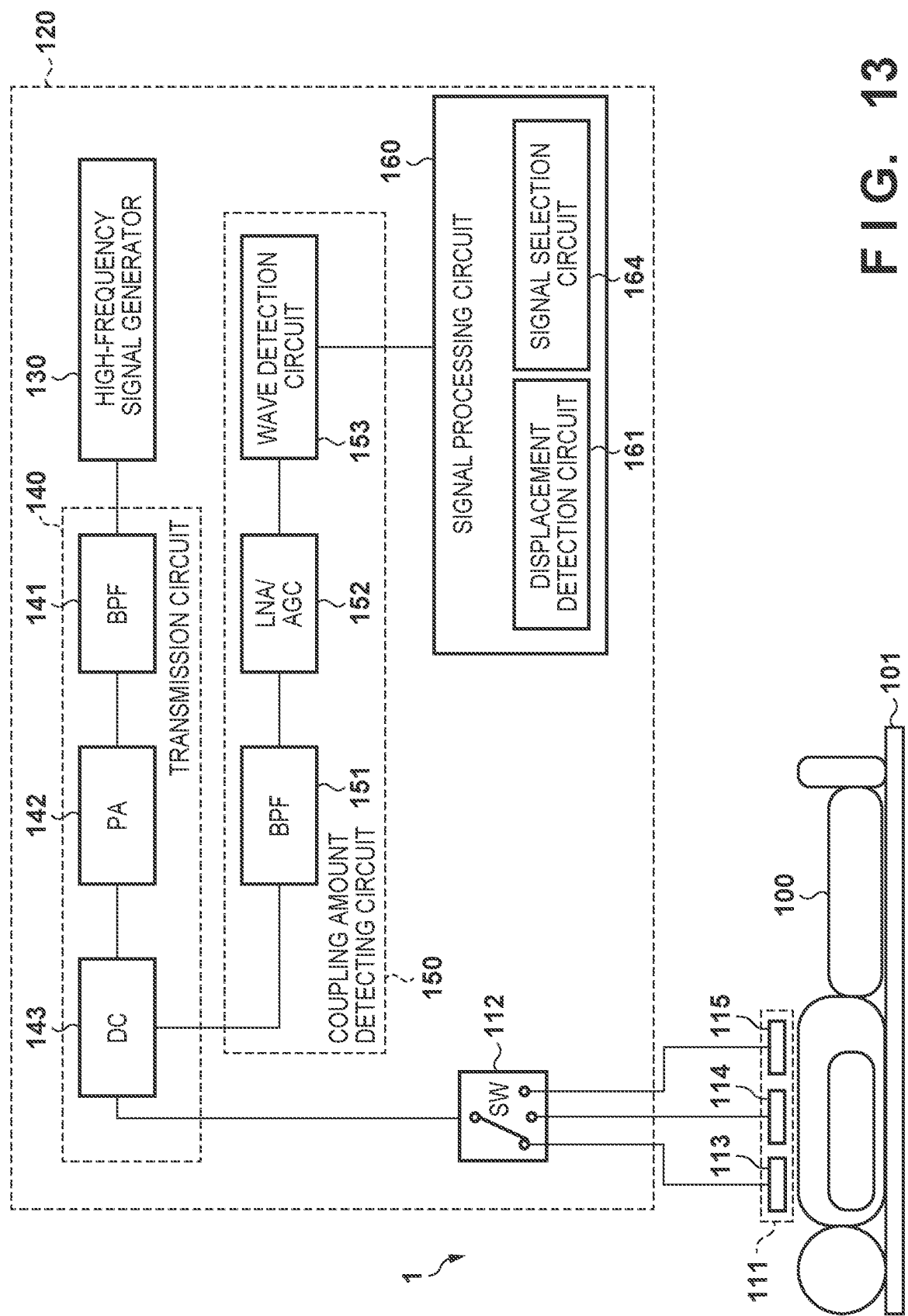
FIG. 13 is a diagram schematically showing a configuration of a subject information acquisition apparatus according to a third embodiment.
Figure 14:
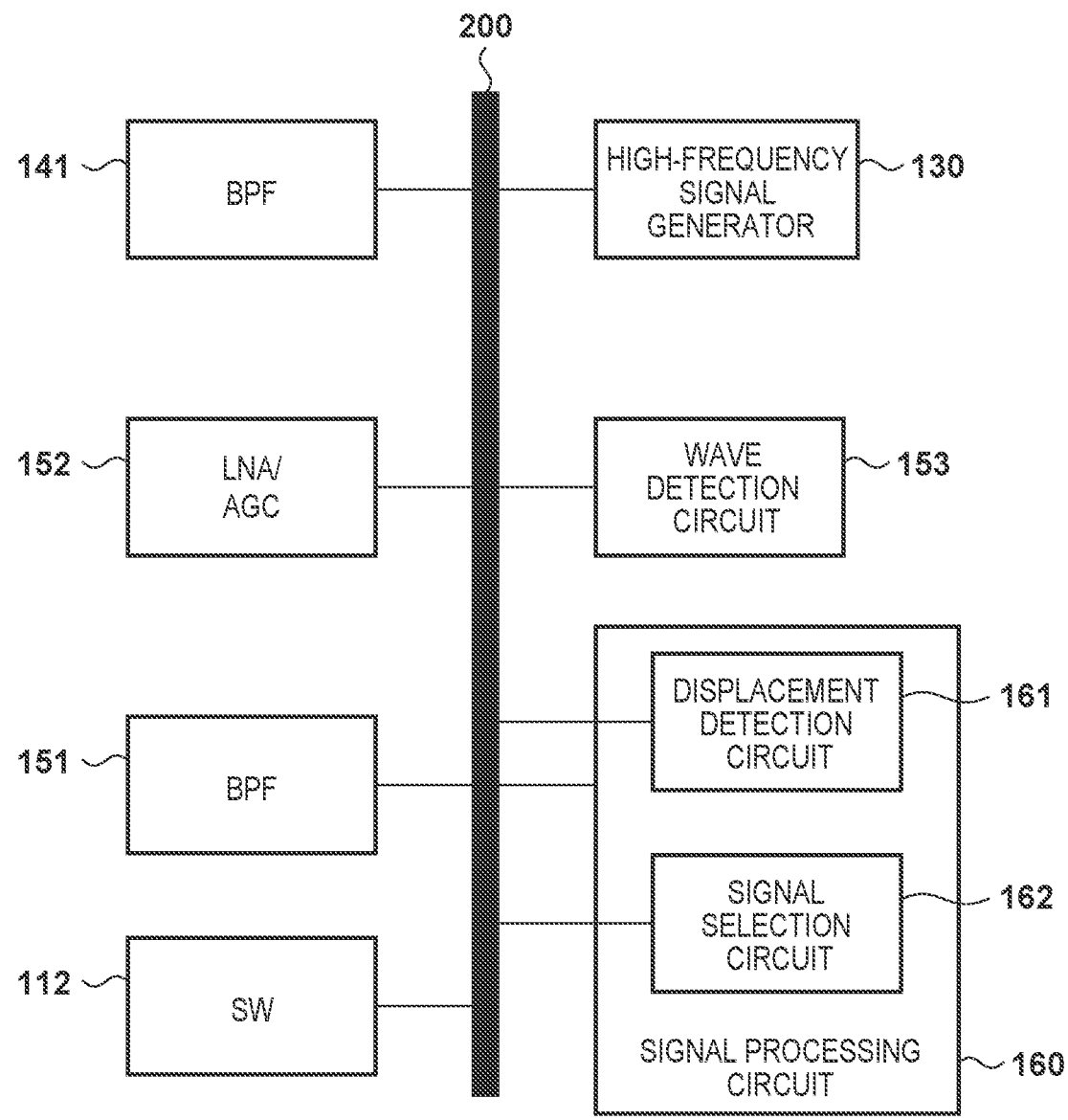
FIG. 14 is a diagram schematically showing a connection relationship of components in the apparatus main body of the third embodiment.

FIG. 13 is a diagram schematically illustrating a configuration of the subject information acquisition apparatus according to the third embodiment, and FIG. 14 is a diagram schematically illustrating a connection relationship of components in the apparatus main body 120 of the third embodiment. Similar to the connection relationship described in the first embodiment, as shown in FIG. 14, each component of the apparatus main body 120 can exchange information via the bus 200, and the signal processing circuit 160 controls operation of each component of the apparatus main body 120 via the bus 200. The connection relationship (FIG. 2) of the components is different to that described in the first embodiment in that an antenna group 111 is configured by a plurality of antennas, and a switching unit for switching the plurality of antennas (hereinafter, a switch (SW) 112) is connected to the bus 200 in FIG. 14.

Antenna Group 111

Different frequencies are set in the high-frequency signal generator 130 and a high-frequency signal corresponding to the respective frequencies is generated. The high-frequency signal generated by the high-frequency signal generator 130 is irradiated to the subject 100 from the antenna group 111 composed of a plurality of antennas. The antenna group 111 includes, for example, a plurality of antennas 113, 114, and 115. The plurality of antennas are arranged to irradiate the high-frequency signal generated by the high-frequency signal generator 130 to different sites of the subject 100. Thus, any one of the plurality of antennas is configured to capture a reflection signal (transmission signal) corresponding to a predetermined movement of the subject 100. Although FIG. 13 exemplarily shows three antennas as the plurality of antennas, the present embodiment is not limited to this example.

In addition, a plurality of antennas may be virtually configured by mechanically scanning a single antenna along the subject 100. For example, the subject information acquisition apparatus 1 may include a scanning unit capable of moving a single antenna in a body axis direction of the subject 100, and may irradiate a high-frequency signal generated by the high-frequency signal generator 130 from the single antenna to a different site of the subject 100 at a position moved to by scanning of the scanning unit.

The plurality of antennas 113, 114, and 115 may be configured to have different shapes depending on the site of the subject 100. For example, a plurality of antennas having different physical lengths and shapes may be disposed so as to irradiate high-frequency signals to the same site. In this case, an antenna having a physical length or shape corresponding to an individual difference of the subject 100, for example, the size of the heart, lung, or abdominal cavity, can be selected from a plurality of antennas.

Switch 112

The switch 112 selects at least one antenna that illuminates a high-frequency signal from each of the antennas 113 to 115 that compose antenna group 111. For example, the switch 112 can select and switch an antenna to be irradiated with a high-frequency signal from the antenna group 111.

It is also possible to set the switch 112 so that high-frequency signals with different frequency settings are irradiated simultaneously from each antenna 113 to 115. The wave detection circuit 153, when detecting the inputted detection signal (input detection signal) based on the simultaneous irradiation of different high-frequency signals, the wave detection circuit 153 separates the input detection signal into detection signals corresponding to the high-frequency signals irradiated from each antenna. In this case, the switch 112 is configured to be virtually switched.

The configuration of the switch 112 may be any configuration, such as an electrical switch or a mechanical switch. The high-frequency signal generator 130, the transmission circuit 140, and the coupling amount detecting circuit 150 may be provided for each of a plurality of antennas constituting the antenna group 111.

Signal Selection Circuit 164

The signal selection circuit 164 of the present embodiment (signal selection unit) selects a signal well-suited for acquiring the subject information from a plurality of detection signals similarly to in the first embodiment (detection signal), but selects a frequency of the high-frequency signal so that it is possible to acquire an index value for each antenna and acquire an optimal detection signal for each antenna. For example, with respect to the antenna 113 near the chest, the signal selection circuit 164 selects a frequency suitable for acquisition of the heart-rate signal. Further, the signal selection circuit 164 can select a frequency suitable for acquisition of the respiration signal with respect to the antennas 114 and 115 in the vicinity of the abdomen.

Further, the signal selection circuit 164 can select an antenna suitable for acquiring a displacement signal corresponding to a predetermined movement of the subject 100 based on the index value of each of the antennas 113 to 115. For the antenna that the signal selection circuit 164 selects, it is possible to select a plurality of the highest ranked antennas in order of largest to smallest acquired index values.

For example, when performing processing based on a plurality of signals such as principal component analysis and independent component analysis in the displacement detection circuit 161, by excluding a low-precision detection signal in which the detection signal corresponding to the predetermined movement of the subject 100 is mostly not included, it is possible to improve precision in the displacement signal that is extracted and reduce the calculation amount. Further, even when the apparatus main body 120 processes the detection signals of all the antennas without selecting an antenna, since the optimum frequency for each antenna is selected by the processing of the signal selection circuit 164, improved precision in the displacement signal that is extracted can be expected.

Method of Acquiring Subject Information

Figure 15:
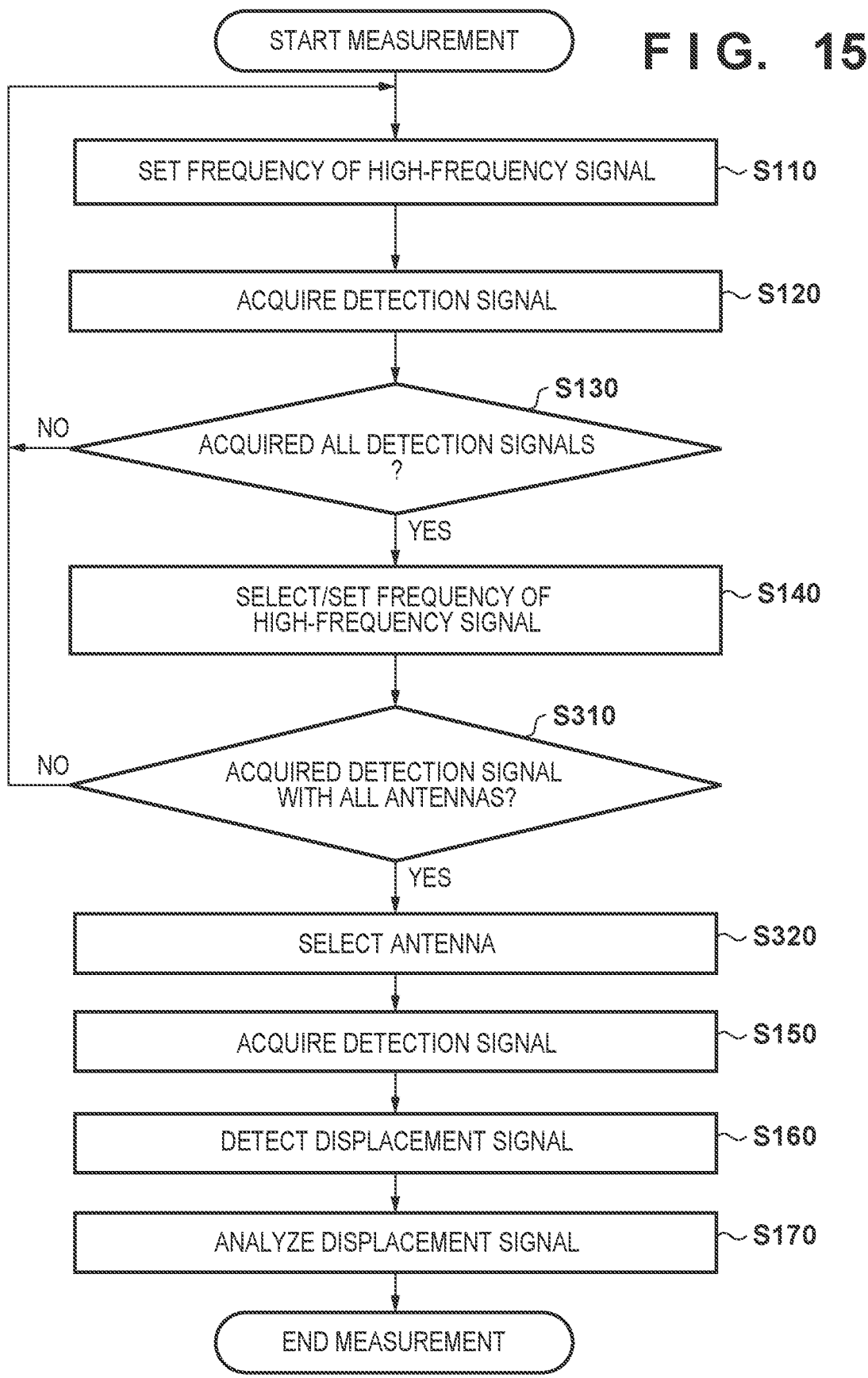
FIG. 15 is a diagram showing a processing flow in the third embodiment.

FIG. 15 is a diagram showing a processing flow in the third embodiment, and each step of the subject information acquisition method according to the present embodiment will be described with reference to FIG. 15. Incidentally, the signal processing circuit 160 executes each step by controlling the operation of each configuration of the apparatus main body 120. Description of the same steps as those in the first embodiment is omitted. The processing of step S110 to step S140 is the same as in the processing flow of the first embodiment (FIG. 7).

Step S310: Step of Determining Whether a Detection Signal Has Been Acquired for All Antennas In this step, the signal processing circuit 160 determines whether the processing for all the antennas 113 to 115 has been completed. That is, the signal processing circuit 160 determines whether the processing for acquiring the detection signal for all the antennas (step S130) and the process for selecting the optimum frequency for each antenna based on the index value of the detection signal (step S140) have been completed. If it is determined that the processing for all antennas has been completed, the signal processing circuit 160 advances the processing to step S320. On the other hand, if it is determined that the processing for all antennas has not been completed, the signal processing circuit 160 returns the processing to step S110.

In the case where processing returns to step S110, the signal processing circuit 160 controls the switch 112 to switch to the next antenna configuring the antenna group 111.

In step S110, the initial value of the frequency range set for each antenna is set to the high-frequency signal generator 130. The signal processing circuit 160 performs the loop processing of step S130 until a detection signal based on the high-frequency signal has been acquired for all frequencies. Then, the signal processing circuit 160 selects the frequency of the optimal high-frequency signal for each antenna based on the index value of the detection signal. The signal processing circuit 160 performs looping of step S310 until the processing for all the antennas 113 to 115 is completed.

Step S320: Step of Selecting the Antenna

In this step, the signal selection circuit 164 selects an antenna for irradiating a high-frequency signal based on the index value for the respective antennas acquired in the step S110 to step S310. For example, the signal selection circuit 164 compares the index value at each antenna, and selects the antenna with the largest index value.

In this step, the signal selection circuit 164 may be select one antenna based on the magnitude of the index value, from the index values for the plurality of antennas, and may select a plurality of the highest ranked antennas in the order of largest to smallest index value.

When the antenna is selected by the signal selection circuit 164, the signal processing circuit 160 controls the switch 112 so that the high-frequency signal is irradiated from the selected antenna.

Further, when a single antenna is moved along the body axis of the subject 100 by a scanning unit, the signal selection circuit 164 may select an irradiation position for irradiating the high-frequency signal based on the index value acquired at each scanning position of the scanning unit, and control the scanning unit to move the antenna to the irradiation position.

If the high-frequency signal generator 130, the transmission circuit 140, and the coupling amount detecting circuit 150 are provided for each antenna, the signal processing circuit 160 selects the high-frequency signal generator 130, the transmission circuit 140, and the coupling amount detecting circuit 150 corresponding to the selected antenna to control operation.

When scanning a single antenna, the signal selection circuit 164 selects the position where the largest index value is obtained as the antenna position based on an index value acquired at each scanning position of the scanning unit which can move the antenna, and the signal selection circuit 164 moves the antenna to the selected antenna position. When all the antennas are used, this step can be omitted.

As described above, according to the present embodiment, by selecting the antenna shape and the measurement site well-suited to acquiring the displacement signal corresponding to the predetermined movement, the movement of the subject can be detected with high accuracy, and the information on the behavior and state of the subject can be acquired with high accuracy.

Fourth Embodiment

In this embodiment, a configuration relating to a magnetic resonance imaging apparatus including a subject information acquisition apparatus according to each of the above-described embodiments will be described.

Configuration of Magnetic Resonance Imaging Apparatus

Figure 16:
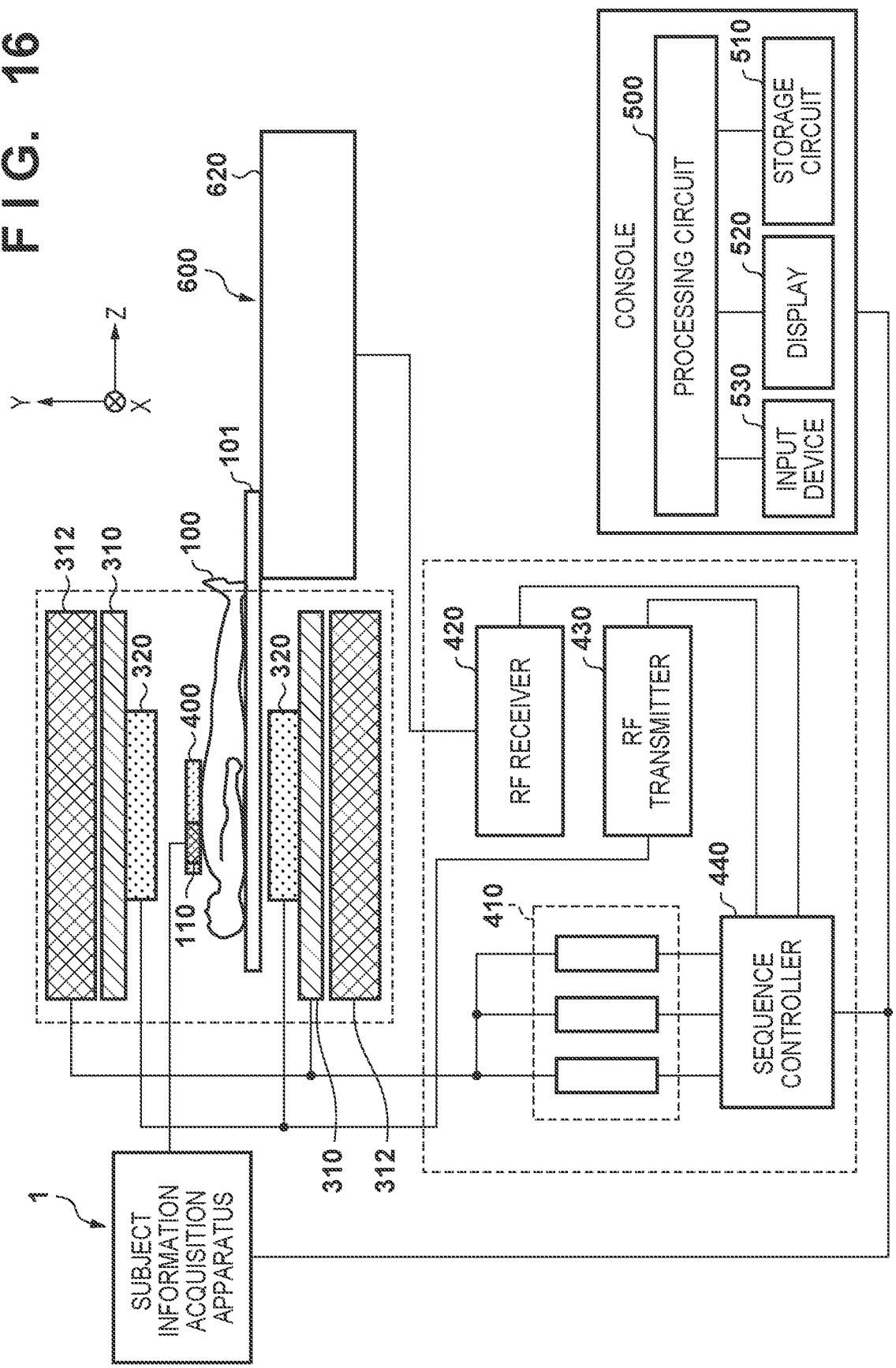
FIG. 16 is a schematic diagram of a magnetic resonance imaging apparatus according to a fourth embodiment.

FIG. 16 is a schematic diagram of a magnetic resonance imaging apparatus according to the present embodiment. The magnetic resonance imaging apparatus has a static magnetic field magnet 312, a gradient magnetic field coil 310, a WB (Whole Body) coil 320 or the like, and these components are housed in a cylindrical housing. The magnetic resonance imaging apparatus further includes a bed 600 including a bed body 620 and a top plate 101, and a local coil 400 disposed in close proximity to the subject 100.

Additionally, the magnetic resonance imaging apparatus includes a gradient magnetic field power supply 410, an RF receiver 420, an RF transmitter 430, and a sequence controller 440. The magnetic resonance imaging apparatus also includes a computer having a processing circuit 500, a storage circuit 510, a display 520, and an input device 530, in other words a console.

The antenna 110 is preferably disposed in close proximity to the subject 100, and is incorporated in the local coil 400 in this embodiment. In addition, the antenna 110 may be disposed inside the top plate 101, or may be disposed close to the subject 100 as a separate device independent of these magnetic resonance imaging apparatuses. Further, a coil provided in a magnetic resonance imaging apparatus such as the gradient magnetic field coil 310 or the WB (Whole Body) coil 320 may be used as the antenna 110.

A processing circuit 500 (imaging control unit) controls the imaging sequence of the magnetic resonance imaging apparatus based on information about the state and behavior of the subject 100 acquired by analyzing the detection signal and the displacement signal outputted from the apparatus main body 120 of the subject information acquisition apparatus 1.

Figure 17:
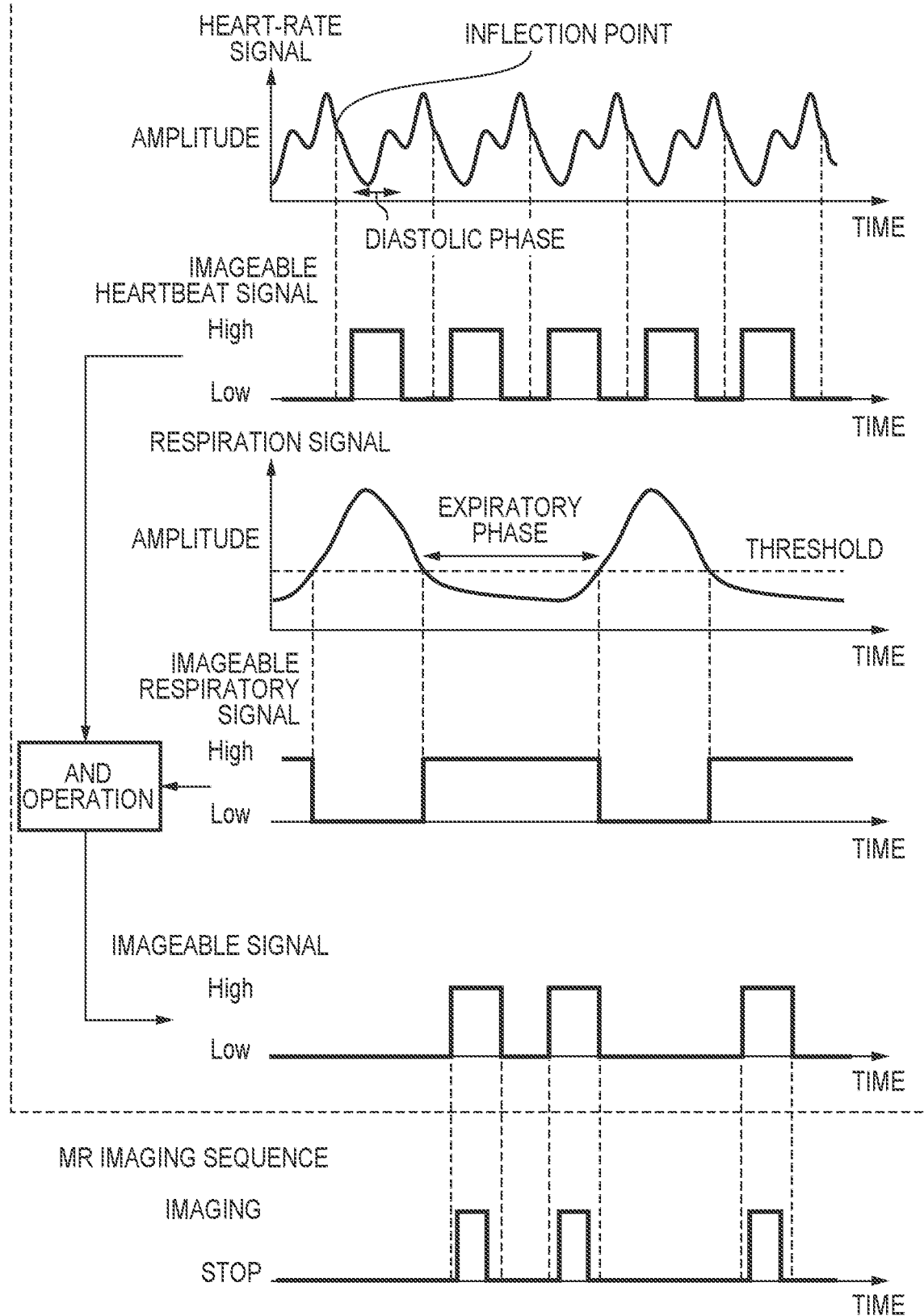
FIG. 17 shows an overview of imaging control in a magnetic resonance imaging apparatus.

FIG. 17 shows an overview of imaging control in a magnetic resonance imaging apparatus. FIG. 17 shows an example of a time phase relationship in the case of controlling an imaging sequence (MR imaging sequence) of the magnetic resonance imaging apparatus using the diastolic phase of the heart-rate signal and the expiratory phase of the respiration signal as information on the state and behavior of the subject 100. As shown in FIG. 4, since the inflection point of the heart-rate signal is close in time phase to the R wave, it becomes the diastolic phase after a predetermined time from the inflection point. A period after a predetermined time has elapsed from the extraction of the inflection point is regarded as the diastolic phase of the heartbeat, and a signal for indicating that it is possible to image a heartbeat for this period is set to high.

In addition, a threshold value is provided for the respiration signal, and a period of time equal to or less than the threshold value can be regarded as the expiratory phase. During the expiratory phase, a signal for indicating that it is possible to image respiration is set to high. Furthermore, an AND operation of a signal for indicating that it is possible to image a heartbeat and a signal for indicating that it is possible to image respiration is performed to generate a signal indicating that imaging is possible. The signal processing circuit 160 executes the above signal processing, and outputs the signal indicating that imaging is possible to the processing circuit 500 of the magnetic resonance imaging apparatus. The processing circuit 500 performs an MR imaging sequence during which the signal indicating that imaging is possible is high. In the diastolic phase, cardiac movement is small, and in the expiratory phase, chest and abdominal movement due to respiration is small. Therefore, by executing an MR imaging sequence during the periods when both signals indicating that imaging is possible are high overlap, it is possible to ameliorate deterioration of the image quality of MR images due to the movement of the subject 100, such as artifacts and resolution deterioration. Further, in the present invention, since the heart-rate signal and the respiration signal can be acquired with high accuracy, the accuracy of signals indicating that imaging is possible generated therefrom is also high, and the image quality of the MR image can be further improved.

Although both the diastolic phase and the expiratory phase have been considered above, a signal indicating that imaging is possible may be based (at least) on only one of the diastolic phase and the expiratory phase. Further, a signal indicating that imaging is possible is not limited to movement due to pulse or respiration, and may be generated based on arbitrary movement of the subject 100.

According to the present embodiment, by controlling the imaging of the magnetic resonance imaging apparatus based on information about the behavior and state of the subject 100 acquired with high accuracy, it is possible to acquire a highly accurate MR image.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2020-206972, filed Dec. 14, 2020, which is hereby incorporated by reference herein in its entirety.

What is claimed is:

1. A subject information acquisition apparatus, comprising:
   a signal generator configured to generate a high-frequency signal corresponding to each of frequencies, wherein different frequencies are set;
   an acquisition circuit configured to acquire a plurality of detection signals based on at least one of a reflection signal and a transmission signal by irradiating the high-frequency signal corresponding to each of the frequencies to a subject from at least one antenna;
   a signal selection circuit configured to select at least one detection signal from the plurality of detection signals based on an index value of the plurality of detection signals;
   a coupling amount detecting circuit configured to detect a coupling amount of near-field coupling due to an electric field between the antenna and the subject based on a detection signal selected in the signal selection circuit; and
   a displacement detecting circuit configured to generate a displacement signal indicating a displacement of the subject based on the coupling amount detected in the coupling amount detecting circuit.

2. The subject information acquisition apparatus according to claim 1, wherein the signal selection circuit is configured to select a frequency of the high-frequency signal corresponding to the selected detection signal, and the signal generator is configured to generate the high-frequency signal based on the frequency selected by the signal selection circuit.

3. The subject information acquisition apparatus according to claim 1, wherein the signal selection circuit is configured to set, as the index value, a similarity between a template signal indicating a signal waveform of a reference and the plurality of detection signals, and is configured to select at least one detection signal from the plurality of detection signals based on the similarity.

4. The subject information acquisition apparatus according to claim 1, wherein the signal selection circuit is configured to set, as the index value, a signal ratio between a signal component indicating the coupling amount and a noise signal component in the plurality of detection signals, and is configured to select at least one detection signal from the plurality of detection signals based on the signal ratio.

5. The subject information acquisition apparatus according to claim 1, further comprising a signal correction circuit configured to correct at least one of the detection signal selected by the signal selection circuit and the displacement signal detected by the displacement detecting circuit.

6. The subject information acquisition apparatus according to claim 5, wherein the signal correction circuit is configured to perform the correction for inverting a sign of the signal.

7. The subject information acquisition apparatus according to claim 6, wherein the signal correction circuit is configured to perform the correction by deconvolving the signal.

8. The subject information acquisition apparatus according to claim 5, wherein the signal correction circuit is configured to correct a value of the signal so as to satisfy the condition regarding the reference value when a condition regarding a value of a signal obtained by statistical processing of the signal is outside of a reference value.

9. The subject information acquisition apparatus according to claim 5, wherein the displacement detecting circuit is configured to generate the displacement signal based on the signal corrected by the signal correction circuit.

10. The subject information acquisition apparatus according to claim 1, further comprising a signal processing unit configured to acquire information indicating movement of the subject based on the displacement signal.

11. The subject information acquisition apparatus according to claim 1, wherein the antenna is configured to irradiate the high-frequency signal generated by the signal generator to different sites of the subject.

12. The subject information acquisition apparatus according to claim 11, further comprising a scanning unit capable of moving a single antenna in line with the subject, wherein
   the high-frequency signal generated by the signal generator is irradiated to a different site of the subject from the single antenna at a position to which the single antenna was moved by scanning of the scanning unit.

13. The subject information acquisition apparatus according to claim 12, wherein the signal selection circuit is configured to select an irradiation position at which to irradiate the high-frequency signal based on the index value acquired at each scanning position of the scanning unit, and
   the antenna is caused to move to the irradiation position by the scanning unit being controlled.

14. The subject information acquisition apparatus according to claim 1, wherein the high-frequency signal generated by the signal generator is irradiated to the subject from a plurality of antennas.

15. The subject information acquisition apparatus according to claim 14, wherein the plurality of antennas have different shapes according to sites of the subject.

16. The subject information acquisition apparatus according to claim 14, wherein the plurality of antennas is arranged so as to irradiate the high-frequency signal to different sites of the subject.

17. The subject information acquisition apparatus according to claim 14, wherein the signal selection circuit is configured to select an antenna for irradiating the high-frequency signal based on an index value at each antenna.

18. A subject information acquisition apparatus, comprising:
   a signal generator configured to generate a high-frequency signal based on a set frequency;
   an acquisition circuit configured to acquire a plurality of detection signals based on a reflection signal or a transmission signal by irradiating the high-frequency signal to a subject from at least one antenna;
   a coupling amount detecting circuit configured to detect a coupling amount of near-field coupling due to an electric field between the antenna and the subject based on the detection signal;
   a displacement detecting circuit configured to generate a displacement signal indicating a displacement of the subject based on the coupling amount detected in the coupling amount detecting circuit; and
   a signal correction circuit configured to correct at least one of the detection signal and the displacement signal detected by the displacement detecting circuit.

19. A magnetic resonance imaging apparatus, comprising:
   the subject information acquisition apparatus according to claim 1; and
   an imaging control unit configured to control an imaging sequence based on a signal outputted from the subject information acquisition apparatus.

20. The subject information acquisition apparatus according to claim 18, wherein the signal correction circuit is configured to correct the value of the signal to satisfy the condition of the reference value when a value of a signal obtained by statistical processing of the signal is outside of a condition regarding a reference value.

21. The subject information acquisition apparatus according to claim 20, wherein the displacement detecting circuit is configured to generate the displacement signal based on the signal corrected by the signal correction circuit.

22. The subject information acquisition apparatus according to claim 18, wherein the signal correction circuit is configured to perform a correction for inverting a sign of the signal.

23. The subject information acquisition apparatus according to claim 18, further comprising a signal processing unit configured to acquire information indicating movement of the subject based on the displacement signal.

24. A subject information acquisition method of a subject information acquisition apparatus, the method comprising:
generating a high-frequency signal corresponding to each of the frequencies, wherein different frequencies are set;
acquiring a plurality of detection signals based on a reflection signal and a transmission signal by irradiating the high-frequency signal corresponding to a respective frequency to a subject from at least one antenna,;
selecting at least one detection signal from the plurality of detection signals based on an index value of the plurality of detection signals;
detecting a coupling amount of near-field coupling due to an electric field between the antenna and the subject based on a detection signal selected in the selecting; and
generating a displacement signal indicating a displacement of the subject based on the coupling amount detected in the coupling amount detecting.

25. A subject information acquisition method of a subject information acquisition apparatus, the method comprising:
generating a high-frequency signal based on a set frequency;
acquiring a detection signal based on a reflection signal or a transmission signal by irradiating the high-frequency signal to a subject from at least one antenna;
detecting a coupling amount of near-field coupling due to an electric field between the antenna and the subject based on the detection signal;
generating a displacement signal indicating a displacement of the subject based on the detected coupling amount; and
correcting at least one of the detection signal and the detected displacement signal.

26. A non-transitory computer-readable storage medium storing a program for causing a computer to perform each step of the subject information acquisition method according to claim 24.

27. A subject information acquisition apparatus, comprising:
a signal generator configured to generate a high-frequency signal corresponding to each of frequencies, wherein different frequencies are set;
an acquisition circuit configured to acquire a plurality of detection signals based on at least one of a reflection signal and a transmission signal by inputting the high-frequency signal corresponding to each of the frequencies to at least one antenna;
a signal selection circuit configured to select at least one detection signal from the plurality of detection signals based on an index value of the plurality of detection signals;
a coupling amount detecting circuit configured to detect a coupling amount of near-field coupling due to an electric field between the antenna and the subject based on a detection signal acquired by inputting a high-frequency signal corresponding to a detection signal selected in the signal selection circuit to the at least one antenna; and
a displacement detecting circuit configured to generate a displacement signal indicating a displacement of the subject based on the coupling amount detected in the coupling amount detecting circuit.

28. A subject information acquisition method of a subject information acquisition apparatus, the method comprising:
generating a high-frequency signal corresponding to each of the frequencies, wherein different frequencies are set;
acquiring a plurality of detection signals based on a reflection signal and a transmission signal by inputting the high-frequency signal corresponding to a respective frequency to at least one antenna;
selecting at least one detection signal from the plurality of detection signals based on an index value of the plurality of detection signals;
detecting a coupling amount of near-field coupling due to an electric field between the antenna and the subject based on a detection signal acquired by inputting a high-frequency signal corresponding to a detection signal selected in the selecting to the at least one antenna; and
generating a displacement signal indicating a displacement of the subject based on the coupling amount detected in the coupling amount detecting.

* * * * *